United States Patent

Brown et al.

[11] Patent Number: 6,140,643
[45] Date of Patent: Oct. 31, 2000

[54] METHOD FOR IDENTIFICATION OF UNKNOWN SUBSTANCES

[75] Inventors: Roy W. Brown, Friendswood; Chul-Sung Kim, Houston, both of Tex.

[73] Assignee: ExxonMobil Upstream Research Company, Houston, Tex.

[21] Appl. No.: 09/265,446

[22] Filed: Mar. 9, 1999

[51] Int. Cl.$^7$ ............................................. G21N 23/225
[52] U.S. Cl. ................... 250/307; 378/48; 702/28
[58] Field of Search ............................ 250/307; 378/48

[56] References Cited

U.S. PATENT DOCUMENTS

| | | | |
|---|---|---|---|
| 4,037,101 | 7/1977 | Okumura et al. | 250/307 |
| 4,797,906 | 1/1989 | Smith | 378/48 |

FOREIGN PATENT DOCUMENTS

| | | | |
|---|---|---|---|
| 2 225 110 | 5/1990 | United Kingdom | G01V 3/12 |

OTHER PUBLICATIONS

Ruisanchez, I.; Potokar, P.; and Zupan, J. Classification of Energy Dispersion X–Ray Spectra of Mineralogical Samples by Artificial Neural Networks, *J. Chem Inf. Comput. Sci.*, 36 (1996), pp. 214–220.

Jeanrot, Pierre. Utilisation En Mineralogie Des Diodes (Si–Li) Associees A La Microscopie Electronique a Balayage, *J. Miscros. Spectrosc. Electron.*, vol. 5 (1980), pp. 99–104.

Jeanrot, Pierre and Remond, Guy. Application de la microscopie électronique á la minéralogie. II. Miscropie électronique á balayage et microanalyse associée par spectrométrie de rayons X dispersive d'énergie, *Bull. Mineral,* 101 (1978), pp. 287–304.

Domitrescu, D.; Pop, Horia F.; and Sârbu. Fuzzy Hierarchiacal Cross–Classification of Greek Muds, *J. Chem Inf. Comput. Sci.*, 35 (1995), pp. 851–857.

Wright, D; Liu, C. L.; Stanley, D.; Chen, H. C.; and Fang, J. H. Xrays: A Fuzzy Expert System for Qualitative XRD Analysis, *Computers & Geosciences*, vol. 19, No. 10 (1993), pp. 1429–1443.

Minnis, Mary Margaret. An Automatic Point–Counting Method for Mineralogical Assessment, *The American Association of Petroleum Geologists Bulletin*, vol. 68, No. 6 (Jun. 1984) pp. 744–752.

Pye, K. Rapid estimation of porosity and mineral abundance in backscattered electron images using a simple SEM image analyser, *Geological Magazine*, No. 121 (2) (1985), pp. 81–84.

Huang, Zehui and Williamson, Mark A. Artificial neural network modelling as an aid to source rock characterization, *Marine and Petroleum Geology*, Vo. 13, No. 2 (1996), pp. 277–290.

(List continued on next page.)

*Primary Examiner*—Jack Berman
*Attorney, Agent, or Firm*—Frank E. Reid

[57] ABSTRACT

The present invention relates to a method for determining the mineral composition of an unknown material using both a fuzzy classification system and a confidence measure of substances identified by the fuzzy classification system. The method can be adapted for identification of pore space and sample points containing more than one material.

19 Claims, 7 Drawing Sheets

OTHER PUBLICATIONS

McCreesh, Catherine A.; Ehrlich, Robert; and Crabtree, Sterling J. Petrography and Reservior Physics II: Relating Thin Section Porosity to Capillary Pressure, the Assocation Between Pore Types and Throat Size, *The American Association of Petroleum Geologists Bulletin*, v. 75, No. 20 (Oct. 1991), pp. 1563–1578.

Lanson, Bruno and Bouchet Alain. Identification Des Mineraux Argileux Par Diffraction Des RayonX: Apport Du Traitement Numérique, *Bull. Centers Rech. Explor.–Prod. El Aquitaine*, V. 19, No. 1 (Jun. 29, 1995), pp. 91–118.

Heilbronner, Renée Panozzo. The autocorrelation function: an image processing tool for fabric analysis, *Tectonophysics*, No. 212 (1992), pp. 351–370. Elsevier Science Publishers B.V., Amsterdam.

Jiang, Wei–Teh and Peacor, Donald R. Transmission and Analytical electron Microscopic Study of Mixed–Layer Illite/Mectite Formed as an Apparent Replacement Product of Diagenetic Illite, *Clays and Clay Minerals*, vol. 38, No. 5, (1990), pp. 449–468.

West, Jeremy. Towards an Expert System for Identification of Minerals in Thin Section, *Mathematical Geology*, vol. 17, No. 7 (1985), pp. 743–753.

Clelland, W. D. and Fens, T. W. Automated Rock Characterization With SEM/Image–Analysis Techniques, Society of Petroleum Engineers, SPE Formation Evaluation (Dec. 1991) 4–37443.

Bondarenko, Igor; Van Espen, Piet; Treiger, Boris; Van Grieken, René; and Adams, Fred. Classification of Coal Mine Dust Particles Through fuzzy Clustering of Their Engery—Dispersive Electron Microprobe X–Ray Spectra, *Microbeam Analysis*, 3 (1994) pp. 33–37.

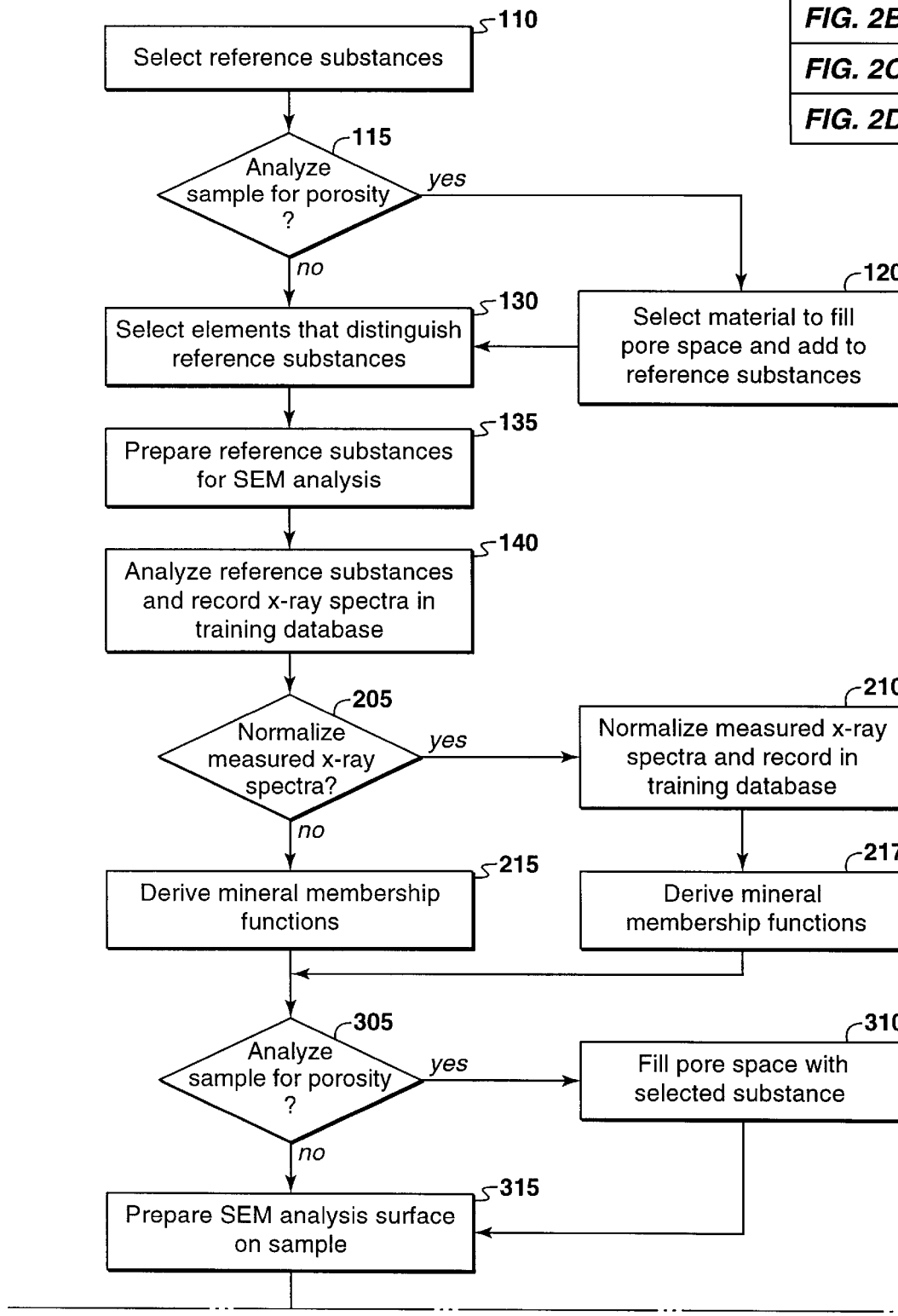

METHOD FOR IDENTIFICATION OF UNKNOWN SUBSTANCES

FIELD OF THE INVENTION

The invention is a method for identification of unknown substances, which is particularly useful in the field of petrography. The method uses a scanning electron microscope and a fuzzy classification system with a confidence measure derived from a set of samples of known substances.

BACKGROUND OF THE INVENTION

Geologic samples are customarily examined using optical petrography to study the mineralogy of the sample. The results of this analysis can be used to estimate the content of various minerals in the sample and further to develop geological interpretations of the depositional and post-depositional processes which formed the sample. In the field of oil and gas exploration, these results are used to help predict the size and quality of underground hydrocarbon reservoirs.

The predominant method of performing optical petrography is "point counting." Notwithstanding improvements in optical lenses and automatic tally counters, optical petrography is still accomplished in essentially the same manner as it was in the 1800's. In this technique, a trained observer, or petrographer, views a magnified image of a rock sample through an optical microscope. The petrographer then classifies the point viewed under the cross-hair in the optical microscope as a specific mineral or pore space by its optical properties and records the observation for that point. The microscope stage is then advanced to additional analysis points, usually in a grid pattern, over the entire sample surface to be examined. The petrographer makes similar assessments at each point in the grid. Upon completion of the grid, the recorded values for each point evaluated are compiled in order to estimate the overall content of various minerals and the porosity in the sample.

There are a variety of problems with this traditional method of point counting. First, even when skilled petrographers are available, mineral estimates by optical petrography are subject to a significant amount of variability. The accuracy and repeatability of each optical identification is dependent upon the individual observer's visual interpretation, training, experience, and fatigue level. The traditional optical process is both tedious and laborious, and disagreement among petrographers is not uncommon.

For example, even the most commonly occurring sedimentary mineral, quartz, can be easily misidentified by an experienced petrographer as albite if it occurs as micro-crystalline quartz. This confusion occurs because it is difficult to distinguish between the optical properties of micro-crystalline quartz and albite when they occur in micrometer grain size. Crystallographic twinning, an optical property of albite, is difficult to observe in grains of this size and therefore not available to aid in distinguishing quartz from albite. This type of misidentification could be important since micro-crystalline quartz is an indicator of solution chemistry in the rock, and as such, may indicate something about the transport properties of the fluid source such as whether or not the source is locally derived. The amount of micro-crystalline quartz can also impact fluid flow properties, such as porosity and permeability, and therefore provide an indication of reservoir quality.

Another difficulty with optical point counting is that some minerals of particular interest to exploration and reservoir geologists occur on a smaller spatial scale than typical optical microscope resolution and may therefore be misidentified. For example, clay minerals have a grain size on the order of approximately 2 micrometers ($\mu$m) or less while resolution of a typical petrographic optical microscope is approximately 20 $\mu$m.

Furthermore, since this work is very tedious and time-consuming, such manual point counting is generally limited to a few hundred points which leads in some cases to an undesirable level of statistical uncertainty. For example, some minerals occur in low abundance (i.e. 5% or less) such that the statistical uncertainty exceeds the absolute content of that mineral in the sample. This level of error can be of great consequence for a mineral that occurs at very low levels yet has a significant effect on reservoir properties. For example, certain clays have a greater impact on fluid flow properties of a rock than others, even though they may occur in equal volume percent. It has been shown that while a certain volume percent of fiberous illite clay will decrease the permeability by over four orders of magnitude from 1000 milli-Darcies to less than 0.1 milli-Darcies, an equal volume percent of kaolinite will decrease the permeability by only two orders magnitude from 1000 milli-Darcies to 40 milli-Darcies. Therefore, misidentification of certain clays could lead to incorrect predictions about the potential productivity of an underground hydrocarbon reservoir.

Porosity estimates are also subject to variability under traditional optical point counting. Geologic samples are typically prepared by impregnating a dyed compound into the pore space of the sample. Blue epoxy is customarily used because few minerals reflect the wavelengths associated with the color blue. In this instance, the accuracy of the porosity estimation depends not only upon the subjective judgment of the petrographer with respect to the intensity of the color but also on the uniformity of the color of the dyed compound.

To reduce the errors and inconsistencies in estimates of the mineral content of geologic samples associated with optical point counting as discussed above, other methods have been proposed for mineral analysis that do not rely upon manual interpretation of visual images. Electron-beam instruments such as the scanning electron microscopes (SEM) and electron microprobes, both equipped with solid state, energy dispersive x-ray detectors (x-ray EDS) can be utilized to determine mineral abundance and porosity without the need for any visual interpretation.

Electron-beam instruments use an electron beam to excite x-ray spectra from the mineral grain by ionizing the atoms of the mineral. The ionized atoms in turn emit x-rays characteristic of their elemental chemistry. An approximation of the concentration of each of the elements in the mineral sample can be derived from the combined x-ray emission, or x-ray spectrum, so generated. The electron-beam-generated x-ray spectrum serves as a chemical fingerprint for each mineral. Such mineral x-ray spectra easily lend themselves to computer pattern recognition techniques, thus reducing the possibility of human error when compared to optical point counting. In addition, the sampling probe on a SEM has a smaller spatial resolution, approximately that of clay grain size (2 $\mu$m), which is about an order of magnitude better resolution than that of the optical petrographic microscope (20 $\mu$m).

A two-step process for mineral analysis based on nonnalized x-ray counts obtained using a SEM and energy-dispersive x-ray micro-analysis is disclosed in Minnis, "An Automatic Point-Counting Method for Mineralogical Assessment," *The American Association of Petroleum*

*Geologists Bulletin,* Vol. 68, No. 6, p. 744–752 (June 1984). The system compares normalized x-ray spectra of a sample of an unknown material to a first set of 20 normalized mineral reference standards each characterized by its content of each of 12 elements. The x-ray spectrum of each point analyzed on the unknown sample is classified by determining the reference standard spectrum nearest the unknown spectrum in 12-dimensional space using an Euclidean distance function. In the second step of this process, the selection made in the first step is compared on a pass/fail basis to a second set of 18 mineral reference standards each characterized by a range of contents of each of 12 elements. Failure to fall within the pre-determined elemental ranges of one of the minerals in this second standard results in a need to further analyze the sample data point to determine whether the spectrum is unclassifiable because the sample point falls on a grain boundary between two minerals, or whether the spectrum is generated by a mineral not a member of the reference set. The disclosure is unclear, however, about how the two reference sets were obtained, and the pass/fail nature of the second step would be very sensitive to small changes in the values of the 12 elements.

Clelland, "Automated Rock Characterization with SEM/Image-Analysis Techniques," *Society of Petroleum Engineers Formation Evaluation,* p. 437–443 (December 1991), discloses a mineral identification system using the combination of a SEM, an energy-dispersive x-ray analyzer, and an image-processing system. As discussed in Minnis, above, the Clelland system also estimates mineral compositions based on comparison of x-ray spectra from an unknown with reference spectra. The disclosure suggests that the use of pseudo-ratios (i.e. assigning fixed values to ratios of element pairs) more effectively addresses statistical fluctuations and slight compositional variations of reference materials than the method of Minnis. This method does not differentiate some very important minerals of similar chemistry (e.g., illite vs. muscovite). Additionally, the Clelland disclosure does not specifically address what is done with points containing mineral mixtures and other unclassifiable points.

Bondarenko, "Classification of Coal Mine Dust Particles through Fuzzy Clustering of Their Energy-Dispersive Electron Microprobe X-ray Spectra," *Microbeam Analysis,* Vol. 3, p. 33–37 (1994), discloses a classification system using fuzzy clustering of x-ray EDS spectra to classify coal mine dust particles. The system disclosed in Bondarenko utilizes rigid threshold values but provides little insight on how to select such values. The disclosure states that the system demonstrated low reproducibility for measurements of some of the selected minerals and suggested that the set of reference minerals used was incomplete due to the high number of unclassified values. This system also provided no confidence measure in final material determinations. Porosity was not addressed at all due to the use of dust samples instead of thin section samples of rock.

Because optical point counting is labor-intensive, tedious, and is subject to human error, the above automated techniques have been proposed to decrease the time required and improve the quality of mineral identification. However, in spite of its inherent difficulties and subjectivity, manual optical petrographic point counting is still the method most widely practiced for estimation of mineral content and porosity. This practice has probably continued since optical petrographic microscopes are less expensive, more numerous, and more transportable to and in the field than many other types of equipment, and traditional university training of petrographers still involves use of these optical techniques.

A need exists for a method which permits objective and reliable identification of unknown substances. Such a method would be a particularly useful tool in the field of oil and gas exploration where estimates of both the type and abundance of various minerals, as well as the porosity, in rock samples are used to help identify valuable hydrocarbon reserves.

SUMMARY OF THE INVENTION

The present invention is a method for determining the composition of an unknown substance using a set of samples of known substances and the x-ray spectroscopy fingerprinting capabilities of a x-ray dispersive (energy or wavelength) analysis system.

First, one or more sample points on a known material are exposed to an electron beam causing the emission of an x-ray spectrum characteristic of the chemistry of each sample point. A database of x-ray spectra is created based upon one or more samples of each of a number of known substances. Reference standards for each known substance and a fuzzy classification system are then derived from the database. The system is described as "fuzzy" because of its ability to effectively classify unknown substances that are close to but outside the limits of the reference standards. The fuzzy classification system consists of substance membership functions for each of the known substances and a confidence measure that judges the reliability of the substance classification made using the substance membership functions. Each substance membership function contains element membership functions which characterize the content of each element in that substance.

After the fuzzy classification system is developed, a sample point on an unknown material is subjected to the same or substantially the same electron beam conditions. The x-ray spectrum so generated is then processed by the fuzzy classification system. The fuzzy classification system determines a candidate substance by selecting the substance whose membership function most closely matches that of the x-ray spectra of the sample point on the unknown material. This candidate substance is then accepted or rejected by use of a confidence measure as correctly identifying the unknown substance contained in the sample point. The confidence measure is a mathematical formula that computes the degree of ambiguity associated with the chosen candidate substance.

In another embodiment, a determination is made whether the point being analyzed on the surface of the sample contains more than one substance based on the presence of a certain signature elements. In cases where such signature elements indicate the presence of multiple substances in the sample point, the point is recorded as containing each of such substances in fractional values summing to one.

In yet another embodiment, in addition to identification of known substances, pore space is identified by impregnating such pore space with a known and distinguishable material prior to measuring the x-ray spectra. This material is then included among the known materials comprising the database from which the fuzzy classification system is derived.

In yet another embodiment, x-ray spectra values for both the known and unknown substances are normalized in addition to using the measured values of certain specified signature elements to identify the presence of a mixture of substances at a sample point.

In yet another embodiment, x-ray spectra are collected from multiple observation points on the sample surface of the unknown material, and the above process steps are repeated for the x-ray spectra from each of the sample points. The assessments of all the sample points are then compiled in order to determine the percentage of each of the known substances contained in the sample.

DESCRIPTION OF THE DRAWINGS

The advantages of the present invention will be better understood by referring to the following detailed description and the attached drawings as described below.

FIGS. 2A–2D set forth a more detailed flowchart of a preferred embodiment of the invention showing optional enhancements to the method.

While the invention will be described in connection with its preferred embodiments, it will be understood that the invention is not limited thereto. On the contrary, the invention is intended to cover all alternatives, modifications, and equivalents which may be included within the spirit and scope of the invention, as defined by the appended claims.

DETAILED DESCRIPTION OF THE INVENTION

The invention is particularly useful in the field of petrography. In a preferred embodiment, the invention consists of an automated point count system for identification of the content of various minerals and the porosity present in a rock sample of an unknown composition. The method is a chemically based system that uses the electron-beam of a SEM to excite x-ray spectra from sample points on the surface of a substance analyzed. In this embodiment, a reference set of known minerals are analyzed to create a training database of normalized x-ray spectra values from which a fuzzy classification system is derived. This preferred embodiment also includes one non-mineral substance in the reference set of known "minerals." This non-mineral substance is used to fill and identify pore space. Then x-ray spectra from analysis points on rock samples of unknown composition are processed by the fuzzy classification system to identify each sample point as one of the reference set of known minerals or as unclassifiable. Repetition of the process and compilation of the analysis results on numerous analysis points results in an estimate of the overall mineral composition and porosity of the sample.

Figure 1:
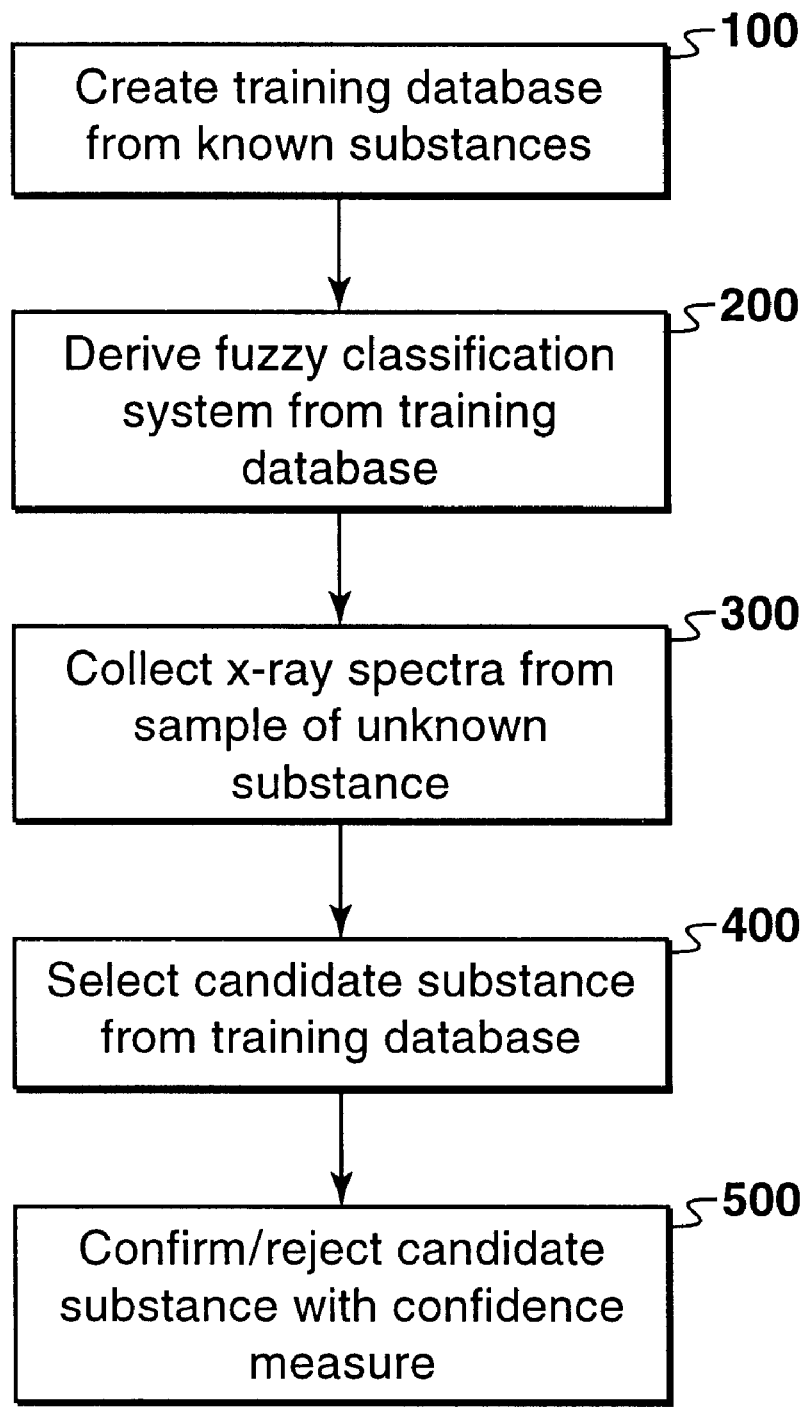
FIG. 1 is a simplified flowchart of the method of the invention.

FIG. 1 is a flowchart illustrating the primary steps of the inventive method for determining the composition of an unknown substance. First, at step 100, a training database of x-ray spectra from at least one sample of each of a plurality of known substances is created. Next, at step 200, a fuzzy classification system is derived from the training database. Preferably, the fuzzy classification system comprises a plurality of substance membership functions wherein each substance is characterized by its content of each of a plurality of pre-selected elements, the content being defined by an element membership function. Next, at step 300, x-ray spectra data from on or more analysis points on a sample of the unknown substance are collected. Next, at step 400, a candidate substance is selected for each analysis point from the plurality of substance membership functions derived at step 200. The candidate substance selected is the substance whose x-ray spectrum data most closely matches that of the analysis point in question. Finally, at step 500, each analysis point is classified as either the candidate substance or an unidentifiable substance using a confidence measure. The foregoing steps of the inventive method are described in greater detail below in connection with FIGS. 2A–2D.

Creation of Database (FIG. 1, item 100)

In order to minimize unnecessary processing of data, it is generally preferable to use whatever information is known about a sample to select reference substances in a manner that reduces the size of the database of reference minerals (FIG. 2A, item 110). For example, geological samples from particular regions and/or strata typically contain a limited number of minerals which are of interest to the one skilled in the art of analyzing such samples. In addition to the types and amounts of minerals present in such a sample, it is also frequently important to determine both the amount and type (i.e. bulk porosity or micro-porosity) of porosity of a sample. To determine porosity (FIG. 2A, item 115), an additional substance, distinguishable from the previously selected minerals, is included in the set of reference substances (FIG. 2A, item 120). After identification of the reference minerals, a set of chemical elements is selected that will permit the members of the reference set to be distinguished from one another (FIG. 2A, item 130).

Therefore, one or more samples of each of a pre-selected number of known minerals, preferably along with a material that will be used to fill the pore space within a sample, define the reference set of known minerals. For purposes of this specification and the appended claims, "m" is an integer representing the number of elements to be considered, "j" is an integer representing a specific element in the set of m elements, "n" is an integer representing the number of minerals to be considered, "i" is an integer representing a specific mineral in the set of n minerals, and "s" indicates a sample of an unknown material.

Preparation of samples of the known substances for SEM analysis (FIG. 2A, item 135) is known to those skilled in the art and typically includes sectioning the sample to create a slice suitably sized for SEM analysis, commonly called a rock thin section. The flat surface of the rock thin section from which measurements will be taken is typically polished to a finish of about 3 $\mu$m, more preferably 1 $\mu$m, even more preferably 0.25 $\mu$m.

After preparation, the reference minerals are analyzed by SEM, and the measured x-ray spectra are recorded in a training database (FIG. 2A, item 140). One or more sample points on the prepared surface of each member of the reference set are exposed to an electron beam. The x-ray spectra for all the sample points analyzed are grouped by mineral. An x-ray spectrum for mineral i of n minerals will be characterized by an intensity, or emission count per unit of time, within certain specific signal ranges as measured in kilo-electron volts (keV). These certain signal ranges are known to indicate the presence of certain elements. The signal intensity within each of these known signal ranges is indicative of the amount of the element associated with that signal range that is present at a selected sample point.

Derivation of Fuzzy Classification System (FIG. 1, item 200)

Preferably, in addition to recording the measured x-ray spectra, normalized x-ray spectra are calculated and recorded (FIG. 2A, item 205). Normalized intensities of the elements in the mineral x-ray EDS spectrum are preferred over measured intensities for use in the element and substance membership functions since the normalized intensities are less dependent on the SEM operating conditions than are the measured, or absolute, intensities. Such operating conditions include but are not limited to electron-beam intensity, accelerating potential, and operating current. The x-ray spectra are normalized by summing the measured intensity for each element of a sample point, dividing the measured intensity for each element j by that sum, and then multiplying each resulting value by a pre-selected constant (FIG. 2A, item 210). This results in a set of normalized spectra that each have an equal total intensity value, meaning that the sum of all element intensities in each normalized spectrum is the same. Normalization of a spectrum is shown mathematically as:

$$x_{i,j} = g\left(\frac{x_{i,j}^r}{\sum_{j=1}^{m} x_{i,j}^r}\right)$$

where $x_{i,j}^r$ is the intensity of element j of a x-ray EDS spectrum for mineral i with the superscript r indicating that a particular value is "as measured", $x_{i,j}$ is the normalized intensity of element j of a normalized x-ray EDS spectrum for mineral i, and g is a constant.

A fuzzy classification system is derived from the training database of x-ray spectra (FIG. 2A, items 215, 217). Although the system will function with as few as one sample of a mineral, it is preferred to have two or more samples of each mineral. Multiple samples of the same mineral, or even multiple sample points on the same sample will, more likely than not, produce slightly different x-ray spectra and are considered multiple samples for purposes of this invention. After the database is complete, mineral membership functions are derived. Each mineral membership function contains an element membership function for each of m elements. Therefore, for a selected mineral i, the training database will contain a range of x-ray intensity values for each element j, each represented as $x_{i,j}$. The maximum value in this range is represented as $x_{i,j}^{max}$ and the minimum value is represented as $x_{i,j}^{min}$.

An element membership function is defined such that any x-ray intensity value falling between or coincident with the maximum and minimum for element j of mineral i is considered to be fully within that membership function and is assigned a numerical value indicating such membership. This numerical value can be any number as long as it is used consistently for all element membership functions, but for simplicity is typically assigned a value of 1.0.

The portion of the element membership function for intensity values less than $x_{i,j}^{min}$ is defined as a pre-selected mathematical or statistical function of the difference between the intensity value and $x_{i,j}^{min}$. Likewise, the portion of the membership function for intensity values greater than $x_{i,j}^{max}$ is a pre-selected mathematical or statistical function of the difference between the intensity value and $x_{i,j}^{max}$. In either case, the value of the membership function decreases as the distance from the relevant endpoint of the range increases. If there is only one sample point for a known mineral, then $x_{i,j}^{max}$ will be equal to $x_{i,j}^{min}$ for each of the m elements.

Preferably, the pre-selected mathematical or statistical relationship is the same for intensity values greater than $x_{i,j}^{max}$ and intensity values less than $x_{i,j}^{min}$. Even more preferably, this relationship is a normal distribution having a standard deviation $\sigma_{i,j}$ that is proportional to the square root of the average of $x_{i,j}^{max}$ and $x_{i,j}^{min}$. This is expressed mathematically as:

$$\sigma_{i,j} = h\sqrt{0.5(x_{i,j}^{max} + x_{i,j}^{min})}$$

wherein

"h" is a preselected constant and preferably, $1 \leq h \leq 2$.

Figure 3:
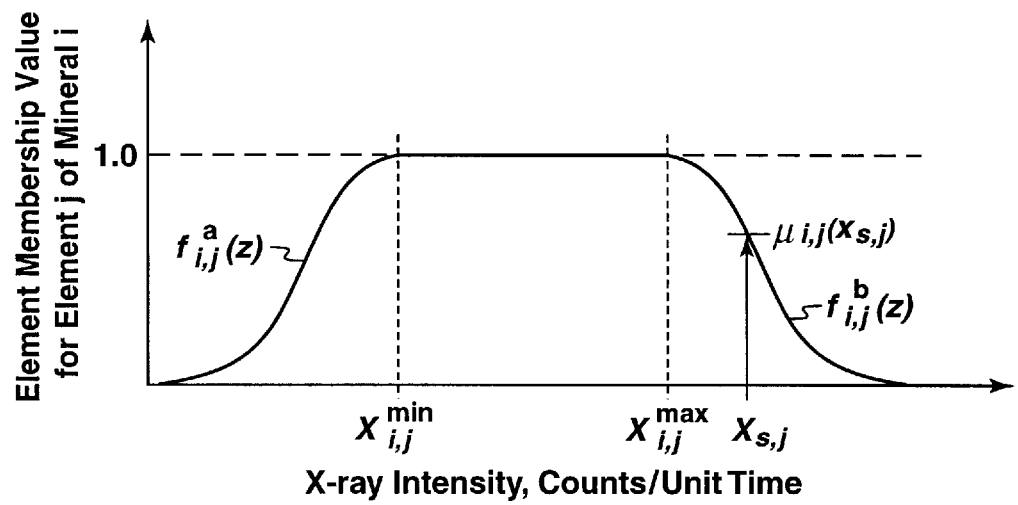
FIG. 3 shows an example of an element membership function that would characterize each of the elements in the substance membership function shown in FIG. 4.

FIG. 3 shows a graphical representation of this preferred embodiment of an element membership function $\mu_{i,j}(x_{i,j})$ for element j of mineral i. The vertical axis shows the magnitude of element membership values $\mu_{i,j}(x_{s,j})$ and the horizontal axis shows x-ray intensity within the spectra range for element j. This relationship is represented mathematically as:

$\mu_{i,j}(x_{s,j})=1.0$, if $x_{i,j}^{min} \leq x_{s,j} \leq x_{i,j}^{max}$ $\mu_{i,j}(x_{s,j})=f_{i,j}^a(z)$ if $x_{s,j} \leq x_{i,j}^{min}$ where, $z=(x_{i,j}^{min}-x_{s,j})$ and, $f_{i,j}^a(z) \leq 1.0$ and decreases as z increases.

$\mu_{i,j}(x_{s,j})=f_{i,j}^a(z)$ if $x_{s,j} > x_{i,j}^{max}$ where, $z=(x_{s,j}-x_{i,j}^{max})$ and, $f_{i,j}^b(z) \leq 1.0$ and decreases as z increases.

In a preferred embodiment:

$$f_{i,j}^a(z) = f_{i,j}^b(z) = \frac{\exp\left(-\frac{z^2}{2\sigma_{i,j}^2}\right)}{\sigma_{i,j}\sqrt{2\pi}}$$

Figure 4:
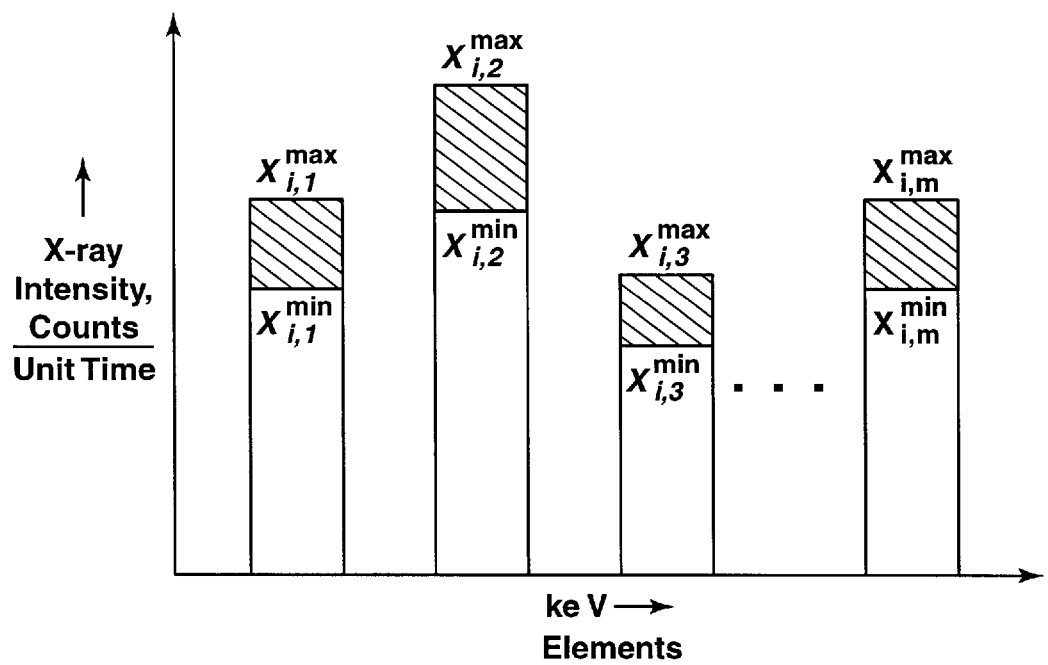
FIG. 4 shows an example of a substance membership function that would be developed from multiple samples of a known mineral.

When taken as a group, the set of all element membership functions, $\mu_{i,j}(x_{s,j})$ for j=1 through m, related to a selected mineral, make up the mineral membership function for that particular mineral i. Each mineral membership function is similar to a x-ray spectrum except that the x-ray intensity in each spectral range, or signal range in keV, known to indicate a particular element is specified by the element membership function for the relevant element instead of by a single x-ray intensity value. FIG. 4 is a graphical representation of a mineral membership function. The shaded area on each element bar indicates the range of values from $x_{i,j}^{min}$ through $x_{i,j}^{max}$ in the training database for that particular element of mineral i. The element membership value for an x-ray intensity value falling within the shaded area is 1.0 and for an x-ray intensity value falling outside the shaded area is defined by $f_{i,j}^a(z)$ and $f_{i,j}^b(z)$ as described above and shown in FIG. 3.

Collection of Sample Data (FIG. 1, item 300)

A sample of an unknown rock is prepared in the same manner as discussed for the samples of known minerals (FIG. 2A, item 315). The rock is sectioned to create a sample specimen sized suitably and having a flat surface suitable for SEM analysis. Where an estimate of the porosity of the sample is desired (FIG. 2A, item 305), the sample preparation includes the additional step, well known to those skilled in the art, of impregnating the free space in the sample to the greatest extent possible with a known substance distinguishable from the reference minerals (FIG. 2A, item 310). This substance is included as one of the minerals in the reference set of known minerals, as discussed earlier.

Figure 2B:
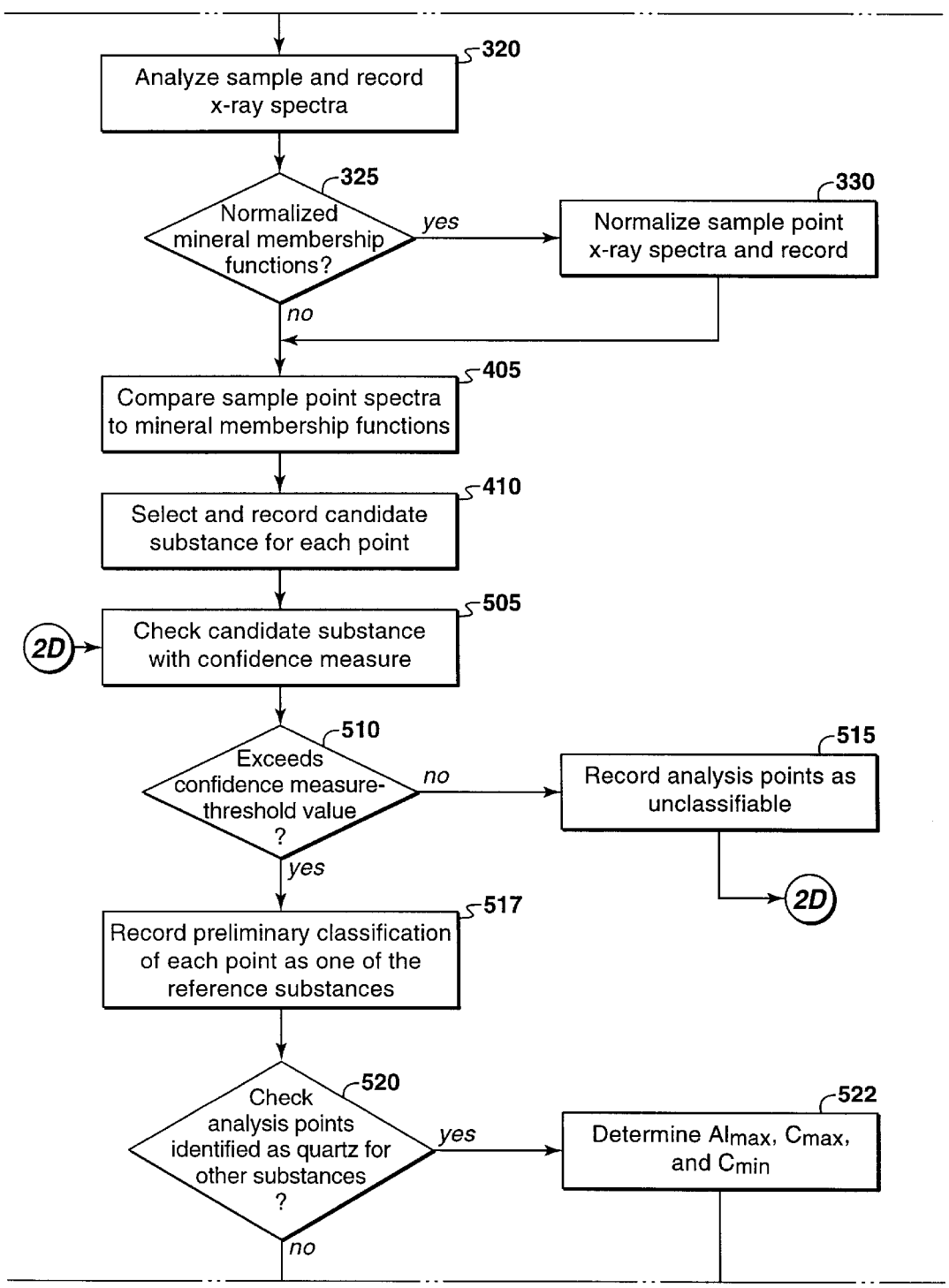

After preparation of the sample, it is placed within the same or substantially similar SEM as was used to develop the training database, and an x-ray spectrum is collected for a selected analysis point on the prepared surface of the sample (FIG. 2B, item 320). Measured sample spectra, and preferably normalized spectra (FIG. 2B, item 325, 330), are recorded in the same way as the spectra in the training database.

Selection of Candidate Substance (FIG. 1, item 400)

Sample point spectra are then compared to the mineral membership functions (FIG. 2B, item 405). A candidate mineral for identification of an individual sample point is selected by determining which mineral membership function most closely matches the x-ray spectrum of the sample point (FIG. 2B, item 410). Preferably, this is a comparison of normalized spectra for both the known and the unknown substances. In any event, when comparing x-ray spectra, a measured or nonnalized spectrum should only be compared to another spectrum of the same type. How well a mineral membership function matches a sample x-ray spectrum is determined by comparing the intensity of the sample x-ray spectrum in each element's spectral range with the element membership function for that element in that mineral membership function. This comparison results in an element membership value according to the relevant element membership function for each element within a selected mineral membership function. A mineral membership value is then calculated for each mineral as the multiplication product of all element membership values for that mineral. The mineral having the maximum mineral membership value becomes the candidate mineral. This relationship is represented mathematically as:

$$\prod_{j=1}^{m}(\mu_{k,j}(x_{s,j})) = \underset{i=1}{\overset{n}{\text{maximum}}}\left(\prod_{j=1}^{m}(\mu_{i,j}(x_{s,j}))\right)$$

k=the value of i that represents the candidate mineral.

Use of Confidence Measure (FIG. 1, item 500)

Classifiers, whether statistical, fuzzy, or based on a neural network, work well if an unknown pattern to be classified, such as an x-ray spectrum, is similar to at least some patterns in the database from which the classifier is derived. This database is sometimes referred to as training data. When an unknown pattern differs greatly from the training data, some of these techniques provide erroneous classification results. Even though the unknown substance is not a good match with any of the known substances, it may still be classified as the one that it most closely matches.

Typically, such classifiers do not provide a method with which to check the accuracy or reliability of the classification. The selection of the candidate substance involves identifying the substance membership function which most closely matches the x-ray spectrum of an analysis point. The classifier of this invention further includes a confidence measure that objectively evaluates whether that "closest" match is also a "good" match (FIG. 2B, item 505). How closely the analysis point x-ray spectrum matches the candidate substance membership function is compared to how closely the analysis point x-ray spectrum matches each of the other substance membership functions. If this mathematical comparison for an analysis point meets or exceeds a selected threshold criteria, then the candidate substance is confirmed. If this comparison fails to meet the threshold criteria, the point is classified as unidentifiable. In a preferred embodiment, the data-based fuzzy classifier of this invention has an explicit confidence measure computation routine. This confidence measure is a nonlinear function of normalized distances in m dimensions between the observed spectrum of the unknown substance and plateau parts of the m element membership functions of each of the n substance membership functions. This relationship is represented mathematically as:

$$CM_k = \left[\sum_{i=1}^{n}\left[\frac{\sum_{j=1}^{m}\left(\frac{d_{k,j}^2}{\sigma_{k,j}^2}\right)}{\sum_{j=1}^{m}\left(\frac{d_{i,j}^2}{\sigma_{i,j}^2}\right)}\right]\right]^{-1},$$

where $CM_k$ is a confidence measure for mineral k, $d_{i,j}$=minimum $(|x_{s,j}-x_{i,j}^{max}|,|x_{s,j}-x_{i,j}^{min}|)$, $d_{k,j}$=minimum $(|x_{s,j}-x_{k,j}^{max}|,|x_{s,j}-x_{k,j}^{min}|)$, $x_{s,j}$ is the intensity of element j of the spectrum of a sample of an unknown substance, $x_{k,j}$ is the intensity of element j of the spectrum of a sample of an unknown substance, $x_{i,j}^{max}$ and $x_{i,j}^{min}$ are the maximum and minimum intensities of element j of the mineral type i observed in the training data, $$\sigma_{i,j} = h\sqrt{0.5(x_{i,j}^{max} + x_{i,j}^{min})},$$

$$\sigma_{k,j} = h\sqrt{0.5(x_{k,j}^{max} + x_{k,j}^{min})},$$

h is a preselected constant and preferably, $1 \leq h \leq 2$, and k is the value of i when the substance membership value is maximized.

This confidence measure $CM_k$ computes the degree of ambiguity in classifying the unknown mineral as mineral k. When the spectra $x_{sj}$ of a sample point of an unknown material is at equal distance to all n mineral spectra patterns in the training database, the confidence measure becomes 1/n. When only two mineral spectra patterns are at equal distance to the spectra $x_{sj}$ and the distance to all other patterns are infinitely large, then confidence measure $CM_k$ assumes the value of 0.5. Therefore, a candidate mineral k with a large value of $CM_k$ has a low ambiguity and a higher probability that the unknown mineral is correctly identified as mineral k. If a candidate mineral k, selected from the fuzzy classifier, has $CM_k$ greater than a certain threshold value (FIG. 2B, item 510), it is considered to be a reliable classification (FIG. 2B, item 517). Otherwise, the x-ray spectrum of the sample point is considered to be not classifiable (FIG. 2B, item 515).

Typically, where the analysis involves 10–20 elements and 30–40 substances, accurate classification of minerals is achieved using a threshold value for $CM_k$ in the range of from 0.1 to 0.3, more preferably in the range of from 0.15 to 0.25, and most preferably when the threshold value is approximately 0.2. A threshold value of 0.2 was found to be preferable in the examples shown below. However, some calibration of the threshold value for particular sets of substances and elements may be required to achieve the desired level of accuracy. Reliability and accuracy of the classification results for individual sample points increases with larger threshold values. However, the number of points found to be unclassifiable will also increase with larger threshold values. Final selection of an optimum threshold value will be based on the standard skills and knowledge available to one skilled in the applicable materials art. This possible iterative process will be discussed further below in the section entitled, Identification of Overall Composition.

In other preferred embodiments, classified points are further evaluated to determine if other minerals and/or pore space are also present. This is performed by identification of "signature elements." Signature elements are elements which are present in one substance in an amount substantially different than in any other reference substance. The signature element may be present in one substance in an amount much greater than that element occurs in the other substances or in an amount much less than the other substances. Therefore, the presence of a signature element of a particular substance in an amount exceeding (or below) the threshold value for that element in that reference set of substances (i.e. exceeds the average or maximum amount or is below the average or minimum amount of that element in all the other substances by a specified margin) indicates that the previously classified point contains both the original candidate substance and the substance containing the signature element. Multiple signature elements can indicate the presence of three or more substances at a single analysis point. Where multiple substances are identified as present in a single analysis point, the point is classified as containing a fractional amount of each of the substance so indicated where the sum of the fractional amounts is one. Depending on the desired precision of the analysis, one skilled in the art could develop methods to more precisely determine such fractional amounts based on linear interpolation related to the intensity (measured or normalized) of the signature element. However, in a preferred simplification of this method, equal fractional amounts of the analysis point are designated as each substance identified.

Figure 2C:
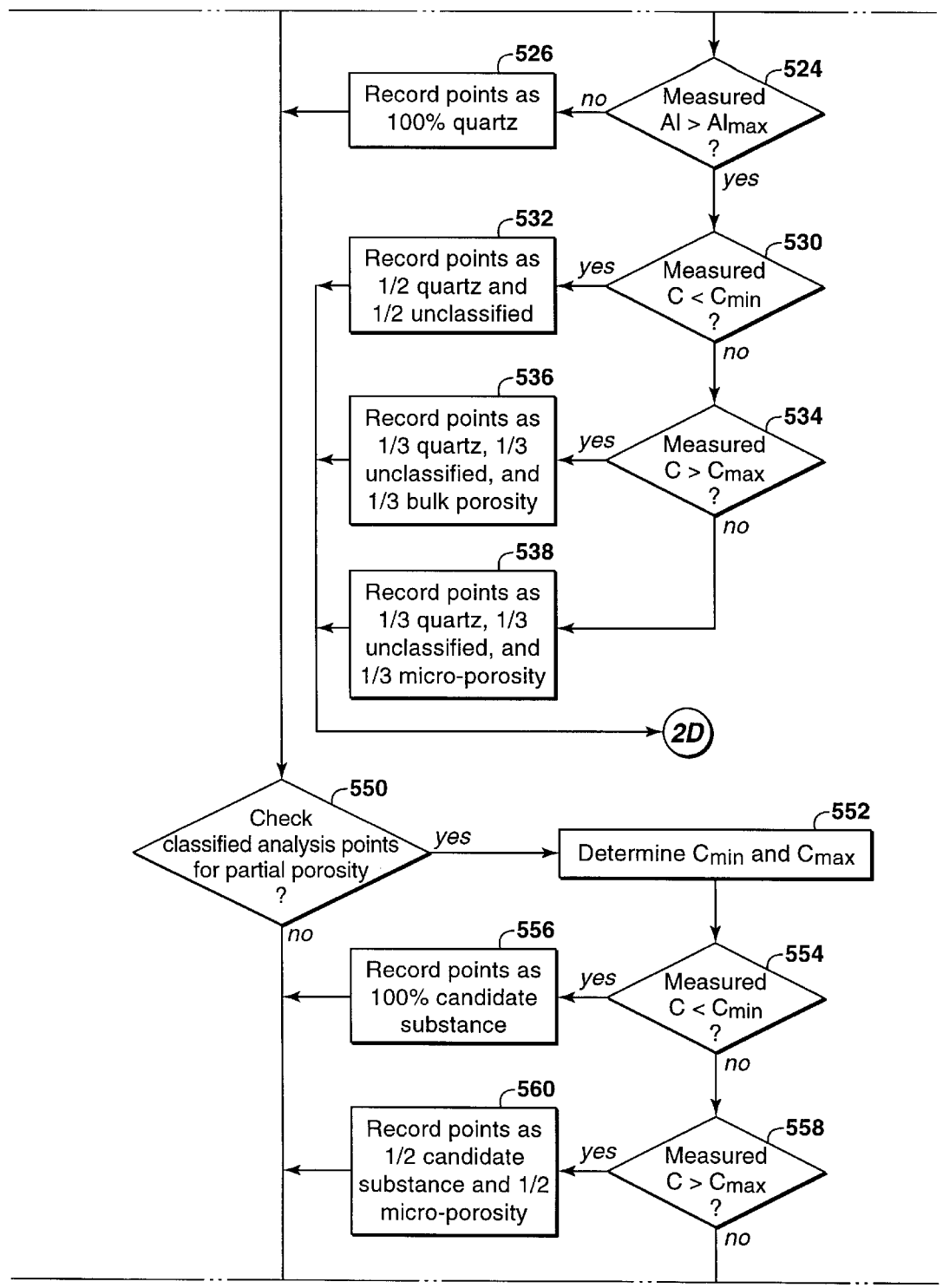

One example of the use of signature elements to identify multiple substances in a single analysis point is shown in FIGS. 2B and 2C, items 520–538. This sub-process was used in the embodiment of the invention described in the Examples section, below. It was determined for the sample materials to be analyzed that it would be desirable to check analysis points identified as quartz for the presence of other minerals or other minerals and porosity (FIG. 2B, item 520). In this sub-process, threshold values of aluminum and carbon intensities are determined (FIG. 2B, item 522) in order to check for the presence of other unidentified minerals or other unidentified minerals and porosity. To determine $Al_{max}$, a normal distribution function and standard deviation (true statistical standard deviation and not σ a as defined for the element membership functions) were calculated for all measured (i.e. not normalized) intensities for aluminum in quartz. $Al_{max}$ was assigned the value of the maximum measured aluminum intensity plus three times the standard deviation all the measured aluminum intensities in quartz. Quartz is relatively free of aluminum. The presence of aluminum in a spectrum classified as quartz in an amount in excess of $Al_{max}$ indicates that the point contains both quartz and a non-quartz mineral. In this instance, $Al_{max}$ is a signature element indicating the presence of a mineral other than quartz. Alternatively, $Al_{max}$ could be calculated from a portion of the reference set that could be mistaken for quartz due to high silicon content. Only the silicate minerals in the reference set are known to have enough silicon content to be misidentified as quartz while having a distinguishably higher aluminum content. The non-silicates in the reference set do not contain significant amounts of either silicon or aluminum. Therefore, $Al_{max}$ using the reference set in the examples could also be calculated as the minimum measured aluminum intensity minus three times the standard deviation of all the measured aluminum intensities for the non-quartz silicate minerals in the reference set.

$C_{max}$ was calculated as the average measured carbon intensity in the carbonate-containing minerals plus the square root of the average measured carbon intensity in the carbonate-containing minerals. An acceptable alternative method for determining $C_{max}$ was calculated from the average measured carbon intensity for all epoxy spectra minus the square root of the average measured carbon intensity for all epoxy spectra. $C_{min}$ was calculated as the average value of all measured carbon intensities for all substances other than epoxy plus the square root of the average value of all measured carbon intensities for all substances other than epoxy.

In this embodiment of this sub-process, if the aluminum intensity of a point with a preliminary classification of quartz does not exceed $Al_{max}$, then the point remains classified as quartz (FIG. 2C, items 524, 526). If the measured aluminum intensity of a point with a preliminary classification of quartz does exceed $Al_{max}$, then the point is classified as part quartz and part non-quartz mineral and is further checked for carbon intensity (FIG. 2C, item 530). If the measured carbon intensity is less than $C_{min}$, then the point is classified as half quartz and half unclassified (i.e. unidentified non-quartz mineral in this case) (FIG. 2C, item 532). If the measured carbon intensity is greater than $C_{min}$, it is then checked against $C_{max}$ (FIG. 2C, item 534). If the measured carbon intensity is greater than $C_{max}$, then the point is classified as one third quartz, one third unclassified, and one third bulk porosity (FIG. 2C, item 536). If the measured carbon intensity is less than $C_{max}$ but greater than $C_{min}$, then the point is classified as one third quartz, one third unclassified, and one third micro-porosity (FIG. 2C, item 538). For purposes of this invention, bulk porosity means continuous pore space on one third of the measured point, while micro-porosity means finely distributed porosity for one third of the point (i.e. ⅓ of the area porous but not continuous). "Finely distributed" porosity, for purposes of geological samples similar to those used in the examples below, means pore space smaller than the size of clay grains, typically less than or equal to 2 μm.

Figure 2D:
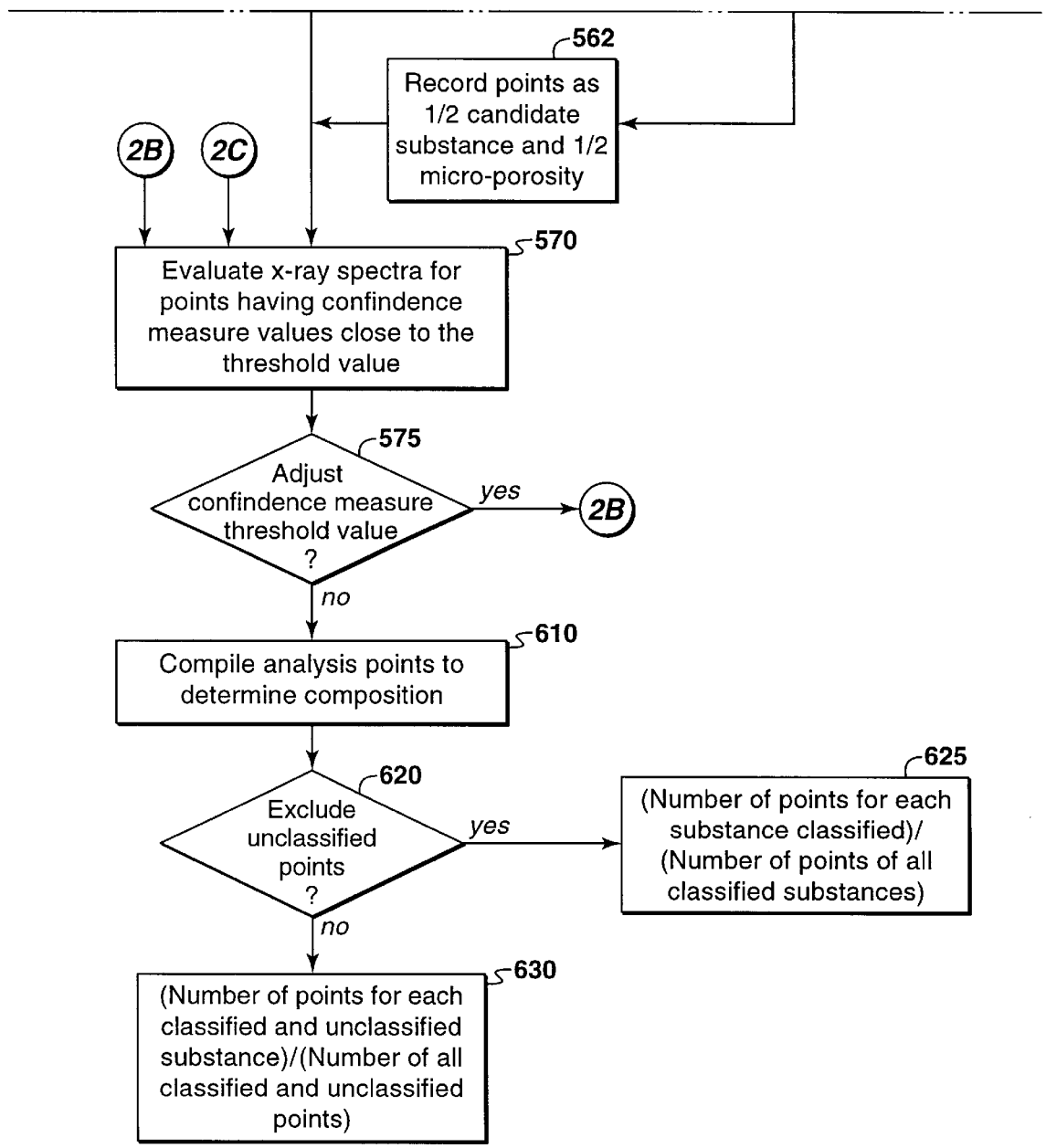

Another example of the use of signature elements to identify multiple substances in a single analysis point is shown in FIGS. 2C and 2D, items 550–562. This sub-process is used if it is determined that it would be desirable to check all analysis points identified as a substance in the reference set (i.e. all points other than those determined to be unclassifiable) for the presence of porosity (FIG. 2C, item 550). In this sub-process, threshold values of carbon intensities are determined (FIG. 2C, item 552) in order to check for the presence and type of porosity. $C_{max}$ and $C_{min}$ are calculated as described above. The minerals in the reference set are relatively free of carbon compared to epoxy.

Therefore, in this embodiment of this sub-process, a point that has a preliminary classification as a mineral but has a measured carbon intensity less than $C_{min}$, then the point remains classified as the original mineral (FIG. 2C, items 554, 556). If the measured carbon intensity is greater than $C_{min}$, it is then checked against $C_{max}$ (FIG. 2C, items 554, 558). If the measured carbon intensity is greater than $C_{max}$, then the point is classified as one half mineral and one half bulk porosity as defined above (FIG. 2C, item 560). If the measured carbon intensity is less than $C_{max}$ but greater than $C_{min}$, then the point is classified as one half mineral and one half micro-porosity as defined above (FIG. 2D, item 562).

At this point, all points have been either classified as one or more substances or determined to be unclassifiable. Prior to compiling the results to estimate the overall composition of the sample, an evaluation of the data is performed by one skilled in the relevant materials art, in this case petrography, to determine the adequacy of the $CM_k$ threshold (FIG. 2D, item 570). Part of the recorded output from the process for each analysis point is a $CM_k$ value whether a point was classified as a substance in the reference set or determined to be unclassifiable. A trained observer reviews the analysis of all classified points having a $CM_k$ value just above the $CM_k$ threshold and all unclassified points having a $CM_k$ value just below the $CM_k$ threshold. Based on a skilled assessment of the nonmalized x-ray spectra of these points, the reviewer will determine whether the $CM_k$ threshold should be adjusted. If it appears that classifiable x-ray spectra have been identified as unclassifiable, the $CM_k$ threshold is reduced. Typically, an initial $CM_k$ threshold value of 0.2 is used. If adjustment of the value is deemed appropriate (FIG. 2D, item 575), the adjusted value is substituted for the previous value. All spectra are then compared to the new $CM_k$ threshold value (i.e. the process is restarted at FIG. 2B, step 505). Once a $CM_k$ threshold value has been set for a particular set of reference substances, the process can be run without the need for expert assistance.

Although this step of the process requires a subjective assessment of a skilled worker, it has many advantages over optical petrography. First, all values are recorded. There is no need to analyze a sample a second time even if adjustments to the final output are later deemed necessary. Second, data collection is objective not subjective. Two experts may have differing opinions about interpreting a x-ray spectra, but factors such as differing visual interpretations and interpreter fatigue level do not occur in this method as they do in optical petrography.

Another simpler method of adjusting the $CM_k$ threshold is to let the system run to a final composition assessment of a sample varying the $CM_k$ threshold in increment of 0.01 with an initial $CM_k$ threshold of 0.2. A $CM_k$ threshold value of 0 would be expected to accept the closest candidate substance identified by the fuzzy classifier for every analysis point even if many are clearly incorrect to an expert's review. A $CM_k$ threshold value that is too high may reject 50% or more of the analysis points as unclassifiable. Testing the range of $CM_k$ threshold values between 0 and 0.5 should yield some range of $CM_k$ threshold values where the total composition estimate is unchanged or changes very little. Picking a $CM_k$ threshold value from this range can then be used in the process for later samples. It is preferable that the normalized x-ray spectra are reviewed at some point in time by an expert as described above to assure the quality of the final composition estimates.

Identification of Overall Composition

In order to develop an estimate of the overall content of various minerals contained in the sample, x-ray spectra are collected from a number of additional selected analysis points. Preferably there arc at least 100 analysis points, more preferably at least 1000 analysis points, even more preferably at least 2000 analysis points. Although the invention can be used with any number of analysis points and statistical accuracy will improve with more analysis points, it is unlikely that the accuracy of the estimate will improve enough to justify gathering x-ray spectra for more than 10,000 analysis points. Preferably the sample points are arranged on an evenly spaced grid pattern in order to facilitate presetting the SEM to automatically advance the SEM through the grid, collecting x-ray spectra at each analysis point. Normalized spectra are also automatically calculated and recorded.

In a preferred embodiment of this invention, data collection is accomplished in an unattended (i.e. without the need for monitoring) mode by computer controlled automation of the SEM microscope stage to move the sample under the electron beam, stopping at points of a predetermined grid pattern to collect x-ray spectra from many data points.

In another preferred embodiment of the invention, data collection is accomplished using user-defined control software that interfaces with manufacturer-supplied software for stage control, beam control, imaging, and x-ray analyzing functions. In one example of this system, with SEM magnification set at 100×, the image area was 2.8 mm$^2$ and was set equal to one frame (2 mm in the x direction and 1.4 mm in the y direction). The range of stage coordinates in the x and y directions and the total number of points to be analyzed were then pre-set by the operator. The control software then calculated the number of frames required to fill the sample area defined by the pre-selected x and y ranges and the number of analysis points per frame required to acquire the total number of pre-set sample data points. The stage was moved by computer-controlled stage automation to each frame position in the evenly spaced grid pattern where computer controlled beam automation moved the beam to each beam position in a random pattern to acquire the number of analysis points required per frame. For each frame, the frame image, stage coordinates, beam coordinates for each random beam position, and x-ray spectra for each point arc all stored in a data file.

To determine overall composition of a sample, the analysis points classified as each of the reference substances as well as the unclassified points are totaled (FIG. 2D, item 610). This will include fractional values if some points were assessed as containing more than one substance. Total porosity is estimated as the sum of all points classified as bulk porosity (i.e. classification of 100% of a point as the substance used to fill the pore space), all partial points classified as bulk porosity, and all partial points classified as micro-porosity. Total porosity can be further broken down as a portion which is bulk porosity and a portion which is micro-porosity. This breakdown can be extremely important in geological assessments of hydrocarbon producibility.

Overall mineral content can be estimated by at least two different methods (FIG. 2D, item 620). In a preferred method, the total number of observation points includes all points classified as identifiable substances and excludes any observation points classified as unidentifiable (FIG. 2D, item 625). The point counts for each identified substance are divided by the total number of identifiable observation points. Overall composition is then reported as a percentage content of each known substance.

In a second method for calculating overall composition of a sample, the total number of observation points includes all observation points classified as a substance in the reference set as well as those that were unclassified (FIG. 2D, item 630). The point counts for each identifiable substance and for the unidentifiable points are divided by the total number of observation points. Overall composition is then reported as a percentage content of each identified substance along with a percentage of unidentified observation points.

Other reporting methods can also be designed as needed. For example, in the field of petrography, results are reported both with and without porosity to aid in the prediction of different qualities of the stratum from which the tested rock was extracted or porosity only may be reported.

EXAMPLES

In a particularly preferred embodiment of this invention, as demonstrated in Examples 1–5, below, the method performed closely followed the flowchart shown in FIG. 2 including: porosity analysis (excluding Example 3; FIG. 2A, items 115, 120, 305, 310), normalization of x-ray spectra for use in mineral membership functions (FIG. 2A, items 205, 210, 217), normalization of the sample x-ray spectra (FIG. 2B, items 325, 330), checking of quartz points for multiple substances (FIGS. 2B and 2C, items 520–538), checking of all points for porosity (FIGS. 2C and 2D, items 550–562), and exclusion of unclassified points (FIG. 2D, items 620, 625). The iterative process (FIG. 2D, items 570 and 575 was used to determine adequate $CM_k$ threshold values.

The fuzzy classification system included the following 35 substances: Quartz, Potassium Feldspar, Albite, Sodium Plagioclase, Calcium Plagioclase, Anorthite, Muscovite, Biotite, Phlogopite, Kaolinite, Illite, Smectite, Low Iron Chlorite, Intermediate Iron Chlorite, High Iron Chlorite, Glauconite, Calcite, Magnesium Calcite, Dolomite, Ankerite, Siderite, Anhydrite, Gypsum, Barite, Pyrite, Pyrrhotite, Apatite, Anatase, Hematite, Zircon, Sphene, Sphalerite, Olivine, Hornblende, and Epoxy.

Each substance was characterized by its content of each of 14 elements: carbon (C), oxygen (O), sodium (Na), magnesium (Mg), aluminum (Al), silicon (Si), phosphorus (P), sulfur (S), chlorine (Cl), potassium (K), calcium (Ca), titanium (Ti), manganese (Mn), and iron (Fe). Of those 35 substances, 34 were associated with minerals found in the sample. The remaining substance was epoxy, which was used to identify the porosity of the samples. The test samples were prepared in the typical manner of preparation for manual petrographic point counting. Free space in the samples was impregnated with epoxy, and the thin sections were polished to a 1 μm finish.

The SEM stage was motorized to move in two dimensions in a plane substantially perpendicular to the direction of the electron beam. Motor speed, motor direction, step size between sampling points, and the number of points traversed in a grid pattern selected by the user were controlled by software commonly included as part of commercially available control system attached to the microscope. The system used in these examples was a JEOL-JSM35C Scanning Electron Microscope (available from JEOL USA, Inc., 11 Dearborn Road, Peabody, Mass. 01960), in conjunction with a Link Analytical eXL—FQAI Micro-analysis System (available from Oxford Instruments, Inc., Analytical Systems Division, 130a Baker Ave. Extension, Concord, Mass. 01742). Similar results using the invention have been achieved using a LEO 435VP Scanning Electron Microscope (available from LEO Electron Microscopy, Inc., One Zeiss Drive, Thornwood, N.Y. 10594), in conjunction with a Link ISIS Quantitative and Imaging Micro-analysis System, Model No. L300QI (available from Oxford Instruments Inc., Analytical Systems Div., 130a Baker Ave. Extension, Concord, Mass. 01742). In either case, the SEM stage is automatically driven throughout the data collection process, stopping at each point to acquire the x-ray spectra characteristic of each point. A software program separate from that controlling the microscope accepted the spectra data and stored it to a file for processing by the classification system of this invention.

The substance membership functions were derived from a training data set of 514 x-ray spectra. Each measured x-ray EDS spectrum was recorded along with a normalized spectrum calculated as follows:

$$x_{i,j} = 1000 \left( \frac{x^r_{i,j}}{\sum_{j=1}^{14} x^r_{i,j}} \right)$$

This training data set contained a variety of x-ray spectrum patterns for each of the 35 minerals of interest. With reference to FIG. 3, all element membership functions in this approach have similar shapes having a flat plateau part in the middle and bell-shaped shoulders at both ends. The plateau part has a membership value of one and is bounded by $x_{i,j}^{max}$ and $x_{i,j}^{min}$, which are the maximum and minimum values of element j of mineral i observed in the training data set. The bell-shaped shoulders are described by a normally distributed probability function whose standard deviation $\sigma_{i,j}$ as shown below:

$$f^a_{i,j}(z) = f^b_{i,j}(z) = \frac{\exp\left(\frac{-z^2}{2\sigma^2_{i,j}}\right)}{\sigma_{i,j}\sqrt{2\pi}}$$

$$\sigma_{i,j} = 1.5\sqrt{\frac{(x^{min}_{i,j} + x^{max}_{i,j})}{2}}$$

A threshold value of 0.2 was used in the confidence measure in order to determine the reliability of the classification.

Example 1
Comparison of the Invention to Optical Point Counting

Table 1 shows mineral analysis data from two samples from Well A which illustrates the improved accuracy of the invention over optical point counting.

TABLE 1

Comparison of the Invention vs. Optical Point Counting (OPC)

| Test No. | 1 | 2 | 3 | 4 | 5 |
|---|---|---|---|---|---|
| Test method | Invention | Invention | OPC | Invention | OPC |
| Sample No. | 1 | 1 | 1 | 2 | 2 |
| Mineral | Vol. % | Vol. % | Vol. % | Vol. % | Vol. % |
| Quartz | 81.2 | 83.8 | 57 | 69.9 | 68 |
| K Feldspar | 0.3 | 0.3 | 0 | 0.1 | — |
| Albite | 2.6 | 1.9 | 2 | 1.8 | 3 |
| Na Plagioclase | 0.5 | 0.3 | — | — | — |
| Muscovite | 0.5 | 0.2 | 1 | 0.5 | — |
| Kaolinite | 0.5 | 0.8 | <1 | 0.8 | 1 |
| Illite | 0.6 | 0.9 | <1 | 0.2 | <1 |
| Smectite | 2.5 | 2.6 | <1 | 0.2 | <1 |
| Glauconite | 0.2 | 0.2 | <1 | — | — |
| Calcite | 0.2 | 0.3 | 0.1 | 0.1 | 1 |
| Ankerite | — | — | — | 0.5 | <1 |

TABLE 1-continued

Comparison of the Invention vs. Optical Point Counting (OPC)

| Test No. | 1 | 2 | 3 | 4 | 5 |
|---|---|---|---|---|---|
| Anatase | — | 0.3 | — | 0.3 | — |
| Pyrite | — | — | — | 0.6 | 0.1 |
| Porosity | 5.4 | 3.7 | — | 19.4 | — |
| Micro-Porosity | 5.4 | 4.5 | — | 5.7 | — |
| Thin Section Porosity | 10.9 | 8.2 | 10 | 25.1 | 18 |
| Gas Porosity | — | — | — | 24.1 | 24.1 |
| Matrix | — | — | 26 | — | 8 |
| No. of Points | 1162 | 1100 | 250 | 935 | 250 |
| $CM_k$ | 0.2 | 0.2 | NA | 0.2 | NA |
| % Points Unclassified | 9.1 | 9.0 | NA | 5.6 | NA |

"—" = not present for minerals or not tested for gas porosity
"NA" = Not applicable Analysis of thin section Sample No. 1 shows a large discrepancy between the results obtained from the method of this invention (Test Nos. 1 and 2) and results obtained from optical point counting (Test No. 3). Of particular note is the difference in the quartz content as measured by the two different methods. The optical petrographic method utilizes a "matrix" category for unidentifiable material. Materials in this category are usually of small grain size, have ambiguous optical properties, and occupy the rock matrix. Matrix is the material filling the space between the framework sand and silt sized grains of the rock. Typically the framework sand has a grain diameter of from about 1/16 mm to 2 mm, and silt sized grains of the rock have grain diameters of from about 1/256 mm to 1/16 mm. Because of small grain size of the matrix material, it is very difficult to identify the mineral using optical techniques. Test No. 3 on Sample No. 1 shows that matrix occupies 26% of the rock according to the optical method. Measurements by the method of this invention do not have a matrix category since chemical fingerprinting of the x-ray spectra is capable of classifying all minerals regardless of optical limitations. This 26% matrix, as analyzed by the optical method, is equal to the quartz difference between the two point count methods. SEM visual examination of a fresh fracture surface of this rock showed micro-crystalline quartz (micrometer and sub-micrometer grain size) filling much of the pore space. Because of the small grain size the matrix material could not be identified as quartz by the optical method. The chemically based method of this invention, with its greater spatial resolution and x-ray spectra pattern recognition capability, identified the matrix material correctly as quartz.

Porosity differences between the two methods are demonstrated by thin section Sample No. 2. The optical method gives a value of 18% for porosity while the method of this invention gives a higher value of 25.1% for the same thin section. The higher porosity percentage reported for Test No. 4 is because the method of this invention is sensitive to the carbon signals generated from micro-porosity (impregnated with epoxy) associated with clay minerals that the optical method is unable to resolve. Epoxy associated with epoxy/mineral mixtures (grain boundaries) is also accounted for by the invention. As a result, the total thin section porosity of 25.1% obtained using the invention compares much more favorably to the gas porosity measurement of 24.1%, than does the 18% as measured by the optical method. Gas porosity, or He porosity, as discussed in this specification refers to the method described in API Recommended Practice for Core-Analysis Procedure, RP 40, 1st ed., August 1960.

Example 2

Comparison of Petrographic Variability and the Method of this Invention

Table 2 shows the variability among three different petrographers using optical point counting on the same polished thin section sample. Petrographers 1a and 1b used a first petrographic accounting system and petrographer 2 used a second petrographic accounting system. Since the method of this invention uses mineral categories and not petrographic categories, inter-method comparison is made using categories of Total Quartz, Total Feldspar, Total Clay and Total Porosity which include all the reported petrographic categories for each mineral. Direct comparison of some mineral categories, such as Plagioclase and Potassic Feldspar, Muscovite, and Pyrite/Marcasite Cement, is also valid.

TABLE 2

Petrographic Variability by Optical Petrography versus the Method of this Invention

| Test No. | 6 | 7 | 8 | 9 |
|---|---|---|---|---|
| Test Method | Petrographer #1a | Petrographer #1b | Petrographer #2 | Invention |
| Sample No. | 3 | 3 | 3 | 3 |
| Petrographic and/or Mineral Category | Vol. % | Vol. % | Vol. % | Vol. % |
| Quartz | — | — | 57.3 | 50.2 |
| Quartz Undifferentiated | — | — | — | NA |
| Quartz Monocrystalline | 34.4 | 38 | — | NA |
| Quartz Polycrystalline | 8 | 5 | — | NA |
| Quartz Overgrowth | 0.4 | 1 | 0.3 | NA |
| Total Quartz | 42.8 | 44 | 57.6 | 50.2 |
| Feldspar Undifferentiated | 12.8 | 6 | — | NA |
| Plagioclase Feldspar | 5.2 | 14 | 1.3 | 4.9 |
| Potassic Feldspar | 2 | 6 | 5 | 7.6 |
| Plutonic Rock Fragment | 1.6 | 2 | — | NA |
| Total Feldspar | 21.6 | 28 | 6.3 | 12.5 |
| Volcanic RK. Frag. Undifferentiated | 9.6 | 7 | — | NA |
| Rock Fragment Undifferentiated | — | — | 1.7 | NA |
| Muscovite | 0.4 | — | — | 0.2 |

TABLE 2-continued

Petrographic Variability by Optical Petrography
versus the Method of this Invention

| Test No. | 6 | 7 | 8 | 9 |
|---|---|---|---|---|
| Biotite | — | — | — | NA |
| Micas Undifferentiated | — | — | 1.3 | NA |
| Heavy Min. & Opaques | — | — | 0.3 | NA |
| Pyrite/Marcasite Cement | 0.4 | — | 1.3 | 0.2 |
| Clay Matrix | 1.2 | — | 1.7 | NA |
| Authigenic Clay Undifferentiated | 18.4 | 12 | 18 | NA |
| Illite | NA | NA | NA | 0.7 |
| Smectite | NA | NA | NA | 0.3 |
| Chlorite | NA | NA | NA | 6.8 |
| Glauconite | NA | NA | NA | 0.4 |
| Total Clay | 19.6 | 12 | 19.7 | 8.2 |
| Intergranular Primary Porosity | 5.2 | 10 | 10.3 | NA |
| Intergranular Secondary Porosity | 0.4 | | 1.3 | NA |
| Total Porosity[1] | 5.6 | 10 | 11.6 | 28.6 |
| Total | 100 | 101 | 99.8 | 99.9 |
| $CM_k$ | NA | NA | NA | 0.2 |
| % Points Unclassified | NA | NA | NA | 6.2 |

[1]He gas porosity = 30.9% by volume
NA = not applicable

The percentage difference for total quartz among the petrographers is 15% in the extreme, with good agreement between petrographers 1a and 1b (1.2% difference). Total Feldspar percentages are quite variable. Petrographer 1a reports twice as much Feldspar Undifferentiated as petrographers 1b, and petrographer 2 reports none. Percentages reported for Plagioclase Feldspar is also variable. Petrographer 1a reports 5.2%, less than half that of the 14% observed by petrographer 1b, while petrographer 2 reports 1.3%, or less than half that of petrographer 1a. Potassic Feldspar reported by petrographers 1a and 1b is 2% and 6%, respectively, with petrographer 2 in close agreement with petrographer 1b at 5%. Therefore, for Potassic Feldspar, two petrographers using different petrographic accounting systems arrived at similar answers, while two petrographers using the same petrographic accounting system obtained different answers. Together quartz and feldspar typically make up the larger framework grains of a rock but they can also occur as small grains, which makes them difficult to distinguish optically. This may be the case for this example as illustrated by the fact that when total quartz and total feldspar are combined, the agreement among two out of three petrographers and the method of this invention is quite good: petrographer 1a reporting 64.4%, petrographer 2 reporting 63.9%, and the method of this invention measuring 62.7%.

Clay percentages show good agreement between petrographers 1a and 2 in both clay categories and in total clay (19.6 and 19.7%, respectively) with Authigenic Clay Undifferentiated the bulk of the clay (18%) for both. Clay matrix category is 1–2% for both. Petrographer 1b reports no Clay matrix and 12% Authigenic Clay Undifferentiated. No clay minerals are specifically identified by any of the three petrographers, e.g. illite, smectite, or chlorite. What was identified by the optical method is really the percentage of fine grained material occupying the rock matrix, which can not be specifically identified by optical methods and, because of its small grain size, is therefore assumed to be clay. It is possible that some of this fine grained material is really Quartz and Feldspar and not Clay minerals.

The bulk of the porosity reported by the three petrographers is the Intergranular Primary Porosity type with petrographer 1a (5%) reporting half of petrographer 1b (10%), and petrographer 2 was in agreement with petrographer 1b. Intergranular Secondary Porosity is reported to be only a small percentage of the total porosity. When compared with He porosity for the rock (30.9%), the method of this invention (28.6%) agrees more closely than does the optical method (6–12%). This is because of the superior resolution of the method of this invention and because it is chemically based and not a color based technique.

Example 3

Synthetic Sandstone Experiment

An attempt to make artificial sandstone containing controlled mixtures of known minerals was performed in this Example as a means of testing the invention's capability to identify and quantify the amount of fibrous illite clay found in the pore volume. Materials used were: quartz from Hot Springs, Arkansas; K (Potassic) Feldspar from Ontario (actually a perthite, or a segregated mixture of K feldspar and Na (Sodium) feldspar); illite from ORD-M; biotite from Canada; and muscovite from Maine, Ontario, or South Dakota (all materials available from 90–91 *Ward's Geology Earth Science Catalog*). Fibrous, freeze-dried illite was run through a typical Deering grinder to break the fibers from a starting size of less than 2 micrometers into smaller pieces prior to mixing with the other minerals.

Sandstone mixtures were prepared by combining specific weight percentages for each mineral. Mixtures were then placed in plastic vials and hand mixed using a rotating motion about the longitudinal vial axis in combination with an end to end rotation of the vial about a centered short axis for three minutes. The mineral mixture was then placed in a tube using a stacking sequence of fine screen material, O-ring, and aluminum-rod plunger at each end of the tube with the mineral mixture in the middle. A compacting force of 110 pounds was applied to the mixture through the aluminum rod ends, for a time of approximately 5 minutes, using a Carver Laboratory Press. The aluminum rods were removed and the tube and mixture, screen and O-rings assembly placed in a cup and vacuum impregnated with blue-dyed epoxy. After the epoxy cured, the impregnated mixture was extracted from the tube and cut length wise into four sections of approximately 1 cm in thickness with a diamond saw. Each section was then mounted on a glass slide, ground and polished using standard petrographic polishing techniques to a finish of 1 micrometer.

The finished product had the appearance of an unconsolidated sand rather than sandstone. There is no guarantee that the synthesized "sandstone" mixtures had uniform composition, that some settling did not occur, or that epoxy vacuum impregnation did not cause some differential mobility of grains due to grain density or morphology difference. Also, it is evident that during grinding and polishing some of the grains were plucked out of the epoxy altering the mixture from its original composition. Therefore, two separate samples from each mixture were analyzed and the results were averaged in order to arrive at the values shown in Table 3. In Mixtures 1 through 4, an amount of one or more of illite, muscovite, biotite, and potassic feldspar was added to the mixture and estimates were made by the method of this invention, as previously described, to determine the mineral content of the sample mixtures. The sample mixtures and the average measured values are shown in Table 3.

Mixtures 1 and 4 also contained 5% by volume muscovite ($K_2Al_4[Si_6Al_2O_{20}]$ $(OH,F)_4$), a potassium mineral very similar to illite and difficult to distinguish from illite by traditional methods. To a large degree the invention was able to distinguish muscovite from illite. Mixtures 2 and 4 also contained biotite and potassium feldspar, respectively, which were correctly identified by the method of the invention as shown in Table 3.

Example 4

Porosity Estimation by the Method of the Invention

Table 4 compares porosity estimates made using the method of this invention and optical petrography with He plug Porosity measurements for nine samples (test method and sample preparation shown in *API Recommended Practice for Core-Analysis Procedure*, API RP 40, First Edition, August 1960).

TABLE 3

Synthetic Sandstone Mixture
vs. Average Analysis by the Invention (Volume %)

| Substance | Mixture 1 | | Mixture 2 | | Mixture 3 | | Mixture 4 | |
| --- | --- | --- | --- | --- | --- | --- | --- | --- |
| Added to Mixture | Vol. % Added | Vol. % Estimated | Vol. % Added | Vol. % Estimated | Vol. % Added | Vol. % Estimated | Vol. % Added | Vol. % Estimated |
| Illite | 5 | 3.9 | 5 | 5.6 | 5 | 4.5 | 5 | 5.1 |
| Muscovite | 5 | 7.5 | 0 | NA | 0 | NA | 5 | 8.6 |
| Biotite | 0 | NA | 5 | 5.7 | 0 | NA | 0 | NA |
| Potassic Feldspar | 0 | NA | 0 | NA | 0 | NA | 10 | 9.4 |

NA = not applicable

All mixtures contained 5% by volume illite ($K_{1-1.5}Al_4$ $[Si_{7-6.5}Al_{1-1.5}O_{20}](OH)_4$). The illite determined by use of the invention ranged from 3.9 to 5.6% with an average of 4.8%.

TABLE 4

Comparison of the Invention Optical
Porosity, and He Porosity (Volume % porosity)

| | Invention | | | | | | | Optical Petrography | | |
| --- | --- | --- | --- | --- | --- | --- | --- | --- | --- | --- |
| Sample | Test No. | | | | | | He | Test No. | | |
| No. | 1 | 2 | 3 | 4 | 5 | Average | Porosity | Average | 1 | 2 | 3 |
| 4 | 16.1 | — | — | — | — | 16.1 | 17.39 | — | — | — | — |
| 5 | 21.6 | 18.8 | — | — | — | 20.2 | 22.14 | — | — | — | — |
| 6 | 13.6 | 11.9 | — | — | — | 12.8 | 16.59 | — | — | — | — |
| 7 | 23.4 | 15.2 | 15.4 | 13.9 | — | 17.0 | 15.23 | — | — | — | — |
| 8 | 19.7 | 18.4 | — | — | — | 19.1 | 24.12 | — | — | — | — |
| 9 | 28.2 | 28.9 | 24.0 | 24.0 | 23.9 | 25.8 | 24.8 | — | — | — | — |
| 10 | 28.6 | — | — | — | — | 28.6 | 30.9 | 9.1 | 5.6 | 10.0 | 11.6 |
| 11 | 25.1 | — | — | — | — | 25.1 | 24.13 | 18.0 | 18.0 | — | — |
| 12 | 15.3 | 15.6 | — | — | — | 15.6 | 17.5 | 9.75 | 9.75 | — | — |

"—" = Not applicable

Tests on Samples 4–12 show comparisons between porosity measurements made by the method of this invention and those made by the He gas porosity method. He porosity is very accurate so it is used as the standard to which the other porosity estimation methods are compared. Both the optical method and the method of this invention are easier to perform, however, since porosity is estimated from samples already prepared for mineral analysis. One to five test runs were made on each sample by the method of this invention. Each test run consisted of about 300 analysis points. The average of all the test runs for each sample are shown in the column next to the He porosity value for each sample to show the accuracy of the invention. The values from each test run are displayed in the columns to the left to illustrate the repeatability of the method of this invention. Also shown for Samples 10–12 are porosity estimates by optical petrography. As with the method of the invention, individual and average test run values are shown where available.

With the exception of tests on Samples 6 and 8, all average values for the method of this invention range from approximately 12% high to 11% low when compared to the He porosity values. The average values by the method of the invention for Samples 6 and 8 were lower than that of He porosity by approximately 23% and 21%, respectively. In contrast, optical porosity estimates ranged from about 25% about 71% lower than the He porosity values. This shows that the method of the invention can more accurately estimate porosity than traditional optical methods.

For Samples 10–12, the same thin sections were measured by use of the invention and by optical methods. The data for Sample 10 also reflects the variability obtained on one thin section by three independent petrographers.

He plug porosity measurements are expected to be greater than values obtained by other methods because one would expect the He gas to get into all connected pore space. Due to different preparation of the samples, He plug and thin section samples are not the same, identical sample. Therefore, the possibility of sample variability exists. One source for variability in porosity results is that the rocks are not completely homogeneous which may result in two samples from the same rock actually having different porosity values. Another source of sample variability could arise during thin section sample preparation. Impregnating the rock with epoxy could cause the rock to fracture, creating additional pore space or the impregnation could be incomplete, not filling all the available pore space. Overall, the porosity values obtained by the method of the invention are significantly closer to He porosity values than those measured by the optical method.

Figure 5:
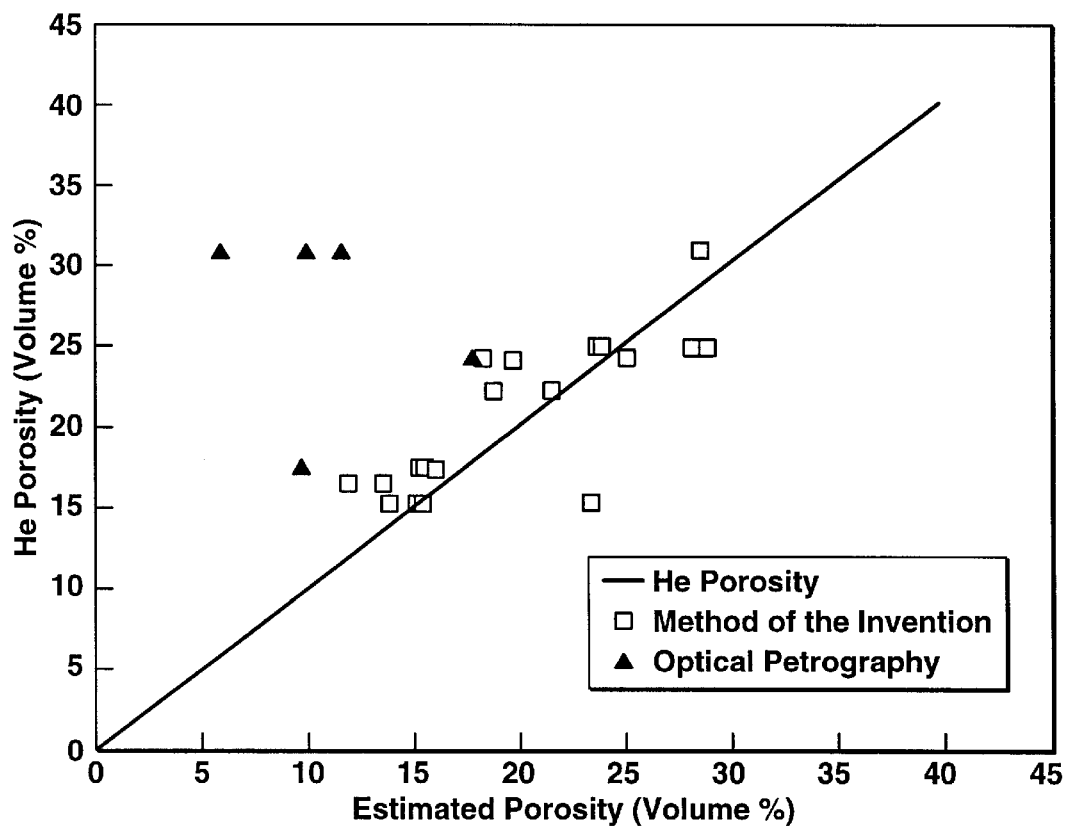
FIG. 5 shows a graphical representation of porosity as estimated by the method of this invention compared to porosity as estimated by optical petrography. Porosity measured by gas permeation is used as a reference standard.

FIG. 5 displays in graphical form the data obtained using the invention and the optical method. For each point, the value on the abscissa is the estimated porosity value and the value on the ordinate is the measured He porosity for a sample of the same material. The line on the chart has a slope of one, representing the line for He porosity values plotted on the abscissa against those same values on the ordinate. The method of the invention more closely conforms to the He porosity line than the optical data and is therefore an improved method for porosity log calibration.

Example 5

Reproducibility of Measured Values

A single polished thin section of 100 milli-Darcy (mD) Berea sandstone was chosen to demonstrate the reproducibility of the invention. This thin section was analyzed 12 times. The number of data points collected varies from 300 to 381 points for each run. In some cases the same stage coordinates were used for several analytical runs because the reproducibility of the SEM stage drives (10 to 50 micrometers) is sufficiently inaccurate to insure that the data collected from the same stage x and y values were in reality different sample points. Table 5 summarizes the analytical results for each of the 12 runs and the average standard deviation for each of 23 minerals identified by the invention during each of the 12 runs. Standard deviation in this instance is not the standard deviation used in the invention but instead the standard statistical value representing the positive square root of the expected value of the square of the difference between a random variable and its mean. After the iterative evaluation process, $CM_k$ was reduced in this cased to near zero and unclassified points ranged from 1.0% to 2.4% of the total points analyzed for each run with and average of 1.6% unclassified for all runs.

TABLE 5

SEM/MIS Measured Mineral Content Reproducibility
(12 runs on 100 mD Berea sandstone; all mineral values in volume %)

| Run No. | 1 | 2 | 3 | 4 | 5 | 6 | 7 | 8 | 9 | 10 | 11 | 12 | Average | Std.Dev. |
|---|---|---|---|---|---|---|---|---|---|---|---|---|---|---|
| Quartz | 68.5 | 70.6 | 69.6 | 71.8 | 69.5 | 64.6 | 70.3 | 69.2 | 71.3 | 71.3 | 69.5 | 65.8 | 69.33 | 2.17 |
| Potassium Feldspar | 3.6 | 3.7 | 4.6 | 3.9 | 4.9 | 4 | 4.1 | 4.3 | 3.1 | 4.6 | 3.1 | 4.6 | 4.04 | 0.59 |
| Albite | 1.6 | 1.5 | 1.4 | 1.7 | 1 | 1.3 | 0 | 0.3 | 0.7 | 0.3 | 0.3 | 1.5 | 0.97 | 0.61 |
| Sodium Plagioclase | 0 | 0.3 | 0.7 | 0 | 0 | 0.3 | 0.3 | 0.3 | 0.3 | 0 | 0.3 | 0.2 | 0.23 | 0.20 |
| Calcium Plagioclase | 0 | 0 | 0.2 | 0 | 0 | 0 | 0 | 0 | 0.3 | 0 | 0.3 | 0 | 0.07 | 0.10 |
| Muscovite | 0.7 | 0.8 | 0.8 | 0.8 | 1.3 | 1.1 | 1.3 | 1.5 | 1 | 1.5 | 1.6 | 2.1 | 1.21 | 0.42 |
| Biotite | 0.3 | 0 | 0.3 | 0 | 0 | 0 | 0 | 0 | 0 | 0 | 0.2 | 0 | 0.07 | 0.12 |
| Kaolinite | 2.3 | 0.7 | 1.9 | 1 | 2 | 3 | 1.1 | 3.3 | 2.8 | 2 | 4.3 | 2.1 | 2.21 | 1.03 |
| Illite | 0.5 | 0.8 | 1 | 0.7 | 0.7 | 0.6 | 0.7 | 0.8 | 0.5 | 0.3 | 2 | 1.3 | 0.83 | 0.45 |
| Smectite | 1.9 | 0.8 | 0.2 | 1.5 | 1 | 1 | 0.8 | 1.7 | 1.7 | 1.6 | 0.8 | 1 | 1.17 | 0.51 |
| Intermediate Iron Chlorite | 0.8 | 0.2 | 0 | 0 | 0 | 0 | 0 | 0 | 0 | 0 | 0 | 0 | 0.08 | 0.23 |
| High Iron Chlorite | 0.4 | 0 | 0.2 | 0.2 | 0.3 | 0.3 | 0.3 | 0.2 | 0 | 0 | 0.7 | 0.2 | 0.23 | 0.20 |
| Glauconite | 0.5 | 0.3 | 0.3 | 0.3 | 0.3 | 0 | 0.3 | 0.3 | 0.3 | 0 | 0.7 | 0.3 | 0.30 | 0.19 |
| Dolomite | 0 | 0 | 0 | 0.2 | 0 | 0 | 0 | 0 | 0 | 0 | 0 | 0 | 0.02 | 0.06 |
| Ankerite | 1.9 | 1.9 | 2 | 1.5 | 2.3 | 2.4 | 1.6 | 1.3 | 2.3 | 1.6 | 1 | 2 | 1.82 | 0.43 |
| Siderite | 0.3 | 0.3 | 0.7 | 0.3 | 0.3 | 1 | 0 | 0.7 | 0.8 | 0.7 | 0 | 0.7 | 0.48 | 0.32 |

TABLE 5-continued

SEM/MIS Measured Mineral Content Reproducibility
(12 runs on 100 mD Berea sandstone; all mineral values in volume %)

| Run No. | 1 | 2 | 3 | 4 | 5 | 6 | 7 | 8 | 9 | 10 | 11 | 12 | Average | Std.Dev. |
|---|---|---|---|---|---|---|---|---|---|---|---|---|---|---|
| Pyrite | 0 | 0 | 0 | 0 | 0 | 0 | 0 | 0.2 | 0.3 | 0 | 0 | 0 | 0.04 | 0.01 |
| Titanium Dioxide | 0.3 | 0 | 0 | 0 | 0 | 0.3 | 0 | 0.5 | 0.2 | 0 | 0 | 0 | 0.11 | 0.17 |
| Zircon | 0 | 0.3 | 0.3 | 0.3 | 0 | 0 | 0.3 | 0 | 0 | 0 | 0.3 | 0 | 0.13 | 0.15 |
| Sphene | 0 | 0 | 0 | 0 | 0 | 0.3 | 0.2 | 0 | 0.3 | 0 | 0 | 0.7 | 0.13 | 0.22 |
| Hornblende | 0 | 0 | 0 | 0 | 0 | 0 | 0 | 0 | 0 | 0 | 0.3 | 0 | 0.03 | 0.09 |
| Epoxy | 12.6 | 14.6 | 12.5 | 13.6 | 12.8 | 15.4 | 16.1 | 11.6 | 10.4 | 11.9 | 11.7 | 13.5 | 13.06 | 1.67 |
| Micro-Porosity | 3.8 | 2.9 | 3.3 | 2.1 | 3.6 | 4.4 | 2.5 | 3.4 | 3.9 | 3.8 | 3.2 | 4.1 | 3.42 | 0.67 |
| Number of Points | 381 | 300 | 300 | 300 | 309 | 316 | 313 | 308 | 308 | 308 | 308 | 308 | 3759 | |

Table 5 represents the variability observed from 12 repeat analyses using the method of this invention on the same thin section sample. The variability is primarily due to the sampling of different points on the thin section. Statistical variation from the x-ray generating and counting process is a negligible contributor to the variation of the overall pattern produced. Table 5 shows that each analysis of the thin section sample produced similar mineralogy. Minerals present at the 5% and lower concentration levels have a larger variability relative to the average percentage for that mineral. Minerals present at the 10% level or greater show a smaller relative variability. This result supports the preference for a higher number of samples than is practical for optical petrography. Even with 300 or more analysis points, the objective chemical fingerprinting of the invention still reflects variability in minerals present at lower concentrations. This variability would be favorably reduced with the higher number of analysis points possible with the invention and impractical with the optical method.

As described above, the present invention provides a method capable of identifying unknown minerals with greater accuracy and reliability relative to traditional optical methods as well as other published techniques. It should be understood that the invention is not to be unduly limited to the foregoing which has been set forth for illustrative purposes. Various modifications and alterations of the invention will be apparent to those skilled in the art without departing from the true scope of the invention as defined in the following claims. Collection and analysis of data may be performed in batch mode at each part or all of the process or each sample point can be run through some or all parts of the process before the next point is processed. Such systems would also have utility in materials identification applications other than geologic compounds.

For example, although the examples above are related to estimation of mineral contents in rock samples, this method would also be useful in measuring chemical segregation in any material where the segregated parts are of unique chemistry detectable by x-ray energy-dispersive or wavelength dispersive spectroscopy. One skilled in the art could prepare samples that could be analyzed by the method of this invention from materials not initially suited for SEM analysis. For example, particulate matter could be mixed with a known and distinguishable matrix substance to that can be hardened into a mass that can be sectioned to create a surface suitable for SEM analysis. The matrix substance could then be subtracted from the analysis results to obtain the composition of the particulate matter.

The experience gathered to date is in the field of mineral and porosity analysis of sedimentary rocks, but the invention could be used in other fields including metallurgy (e.g. phase segregation and/or inclusions in alloys or chemical heterogeneity of alloys), composite materials (e.g. phase distribution in composites), concrete chemistry, and environmental pollution analysis (e.g. identification of particulate in air pollution samples). The method would be useful for identification of unknown materials of any type provided that a finite set of known substances is available for development of a database. To the extent that each of the substances in the database is identified by a greater number of elements in distinguishable amounts, the method will work better.

What is claimed is:

1. A method for determining the composition of an unknown substance comprising the steps of:
   1) creating a database of x-ray spectra from at least one sample of each of a plurality of known substances,
   2) deriving a fuzzy classification system from said database, said system comprising a plurality of substance membership functions wherein each substance is characterized by its content of each of a plurality of pre-selected elements, said content being defined by an element membership function,
   3) collecting x-ray spectrum data from one or more analysis points on a sample of said unknown substance,
   4) selecting for each of said analysis point a candidate substance from said plurality of substance membership functions which most closely matches the x-ray spectrum data of said observation point, and
   5) classifying each said analysis point as either said candidate substance or an unidentifiable substance using a confidence measure.

2. The method of claim 1 wherein said x-ray spectra from said known substances are normalized for use in deriving said substance membership functions and said x-ray spectrum data collected from said one or more analysis points are normalized for comparison to said substance membership functions.

3. The method of claim 1 wherein porosity is determined by filling pore space in said unknown substance with a filler material included in said plurality of known substances.

4. The method of claim 1 wherein said known substances comprise one or more substances each containing one or more signature elements, said method further comprising the steps of:
   1) calculating a threshold value for each said signature element, 2) determining whether each said analysis point identified as containing said candidate substance also contains said one or more substances containing signature elements based on comparison of the content of said each said signature element to each said threshold, and 3) changing said classification of each said analysis point containing more than one substance to fractional amounts of said analysis point each classified as one of said candidate substance and said one or more substances containing said signature element, wherein the sum of said fractional amounts is one.

5. The method of claim 4 wherein said known substances include a first substance having an element membership function minimum intensity for a first signature element higher than a first threshold value for said first signature element, and the maximum intensity of the element membership function for said first signature element for any of the other known substances is below said threshold value for said first signature element.

6. The method of claim 5 wherein said first substance is a filler material used to identify porosity.

7. The method of claim 6 wherein a second threshold for said first signature element is calculated and is greater than the maximum intensity of the element membership function for said first signature element for any of said other known substances but less than said first threshold for said first signature element.

8. The method of claim 7 wherein:
   a) each said analysis point having an x-ray intensity for said first signature element greater than said first threshold for said first signature element is classified as a fractional amount of said candidate substance and a fractional amount of bulk porosity,
   b) each said analysis point having an x-ray intensity for said first signature element greater than said second threshold but less than said first threshold for said first signature element is classified as a fractional amount of said candidate substance and a fractional amount of micro-porosity, and
   c) each said analysis point having an x-ray intensity for said first signature element less than said second threshold for said first signature element remains classified as said candidate substance.

9. The method of claim 4 wherein said known substances include a second substance having an element membership function maximum intensity for a second signature element lower than a first threshold value for said second signature element, and the minimum intensity of the element membership function for said second signature element for any of the other known substances is greater than said first threshold value for said second signature element.

10. The method of claim 9 wherein:
   a) each said analysis point having an x-ray intensity for said second signature element greater than said first threshold for said second signature element is classified as a fractional amount of said candidate substance and a fractional amount of unclassifiable substance, and
   b) each said analysis point having an x-ray intensity for said second signature element less than said first threshold for said second signature element remains classified as said candidate substance.

11. The method of claim 4 wherein said known substances include:
   a) a first substance having an element membership function minimum intensity for a first signature element higher than a first threshold value for said first signature element, and the maximum intensity of the element membership function for said first signature element for any of the other known substances is below said threshold value for said first signature element, and
   b) a second substance having an element membership function maximum intensity for a second signature element lower than a threshold value for said second signature element, and the minimum intensity of the element membership function for said second signature element for any of the other known substances is greater than said first threshold value for said second signature element.

12. The method of claim 1 further comprising the step of calculating an estimate of the overall content of each of said known substances present in said sample of said unknown substance by dividing the number of analysis points identified as each known substance or as unidentifiable by the total number of analysis points.

13. The method of claim 1 further comprising the step of calculating an estimate of the overall content of each of said known substances present in said sample of said unknown substance by dividing the number of analysis points identified as each known substance by the total number of analysis points identified as any of the known substances.

14. The method of claim 1 wherein said step of selecting the candidate substance is defined by the equation:

$$\prod_{j=1}^{m} (\mu_{k,j}(x_{s,j})) = \operatorname*{maximum}_{i=1}^{n}\left(\prod_{j=1}^{m} (\mu_{i,j}(x_{s,j}))\right)$$

wherein k = the value of i that represents the candidate substance, $\mu_{i,j}(x_{s,j}) = 1$ if $x_{i,j}^{min} \leq x_{s,j} \leq x_{i,j}^{max}$, $\mu_{i,j}(x_{s,j}) = f_{i,j}^{a}(x_{i,j}^{min} - x_{s,j})$ if $x_{s,j} < x_{i,j}^{min}$, $\mu_{i,j}(x_{s,j}) = f_{i,j}^{b}(x_{s,j} - x_{i,j}^{max})$ if $x_{s,j} > x_{i,j}^{max}$, $f_{i,j}^{a}(z) = 1$ and $f_{i,j}^{b}(z) = 1$ if $z = 0$, $f_{i,j}^{a}(z) \leq 1$ and $f_{i,j}^{b}(z) \leq 1$ and both decrease as $|z|$ increases, "m" is an integer defining the number of elements in the x-ray spectra, "n" is an integer defining the number of substances in the database, "i" is an integer from 1 to n identifying the subscripted variable as associated with a specific substance from said pre-selected set of substances, "j" is an integer from 1 to m identifying the subscripted variable as associated with a specific element from said pre-selected set of elements, "s" in subscripts indicates that the value of the subscripted variable is associated with said unknown substance, and "x" is an x-ray spectrum intensity value.

15. The method of claim 14 wherein $f_{i,j}^{a}(z)$ and $f_{i,j}^{b}(z)$ are normally distributed probability functions having a standard deviation, $\sigma_{i,j}$ defined by the equation $$\sigma_{i,j} = h\sqrt{0.5(x_{i,j}^{max} + x_{i,j}^{min})}$$

wherein h is a pre-selected constant.

16. The method of claim 1 wherein said process of using confidence measure comprises the steps of calculating the value of a confidence measure equation for said candidate substance and comparing said value to a threshold value, wherein said confidence measure equation is:

$$CM_k = \left[ \sum_{i=1}^{n} \left( \frac{\sum_{j=1}^{m} \left( \frac{d_{k,j}^2}{\sigma_{k,j}^2} \right)}{\sum_{j=1}^{m} \left( \frac{d_{i,j}^2}{\sigma_{i,j}^2} \right)} \right) \right]^{-1}$$

wherein $d_{k,j}$=minimum($|x_{s,j}-x_{k,j}^{max}|, |x_{s,j}-x_{k,j}^{min}|$), $d_{i,j}$=minimum($|x_{s,j}-x_{i,j}^{max}|, |x_{s,j}-x_{i,j}^{min}|$), $$\sigma_{i,j} = 1.5\sqrt{0.5(x_{i,j}^{max} + x_{i,j}^{min})},$$

$$\sigma_{k,j} = 1.5\sqrt{0.5(x_{k,j}^{max} + x_{k,j}^{min})},$$

"CM" is the confidence measure,

"m" is an integer defining the number of elements in the x-ray spectra,

"n" is an integer defining the number of substances in the database,

"i" is an integer from 1 to n identifying the subscripted variable as associated with a specific substance from said pre-selected set of substances, "j" is an integer from 1 to m identifying the subscripted variable as associated with a specific element from said pre-selected set of elements, "k" is an integer identifying the subscripted variable as associated with the candidate substance, "s" in subscripts indicates that the value of the subscripted variable is associated with said unknown substance, and "x" is an x-ray spectrum intensity value.

17. A method for determining the composition of an unknown geological sample, said method comprising the steps of:

1) creating a training database of normalized x-ray spectra for at least one sample of each of a plurality of known minerals, 2) deriving a fuzzy classification system from said database, said system comprising a plurality of substance membership functions wherein each substance is characterized by its content of each of a plurality of pre-selected elements, one of which is carbon, said content being defined by an element membership function, 3) collecting x-ray spectrum data, recording measured and calculating normalized values, from a plurality of observation points on a sample of said unknown material, wherein said sample is a geologic sample having a polished surface, prepared by impregnating into the pore space of said sample an epoxy material containing carbon as a signature element, 7) selecting a candidate substance for each said observation points from said plurality of substance membership functions which most closely matches the normalized x-ray spectrum data of said observation point, 8) classifying each said observation point as either said candidate substance or an unidentifiable material using a confidence measure, 9) determining, for each said observation point classified as a candidate substance, whether one or more of the other known substances is also present by comparing measured x-ray intensities of signature elements at each said said observation point to threshold values for each said signature element, and reclassifying observation points determined to contain more than one substance as fractional portions, summing to one, of each substance so identified; and 10) calculating the overall content of each substance in said sample of said unknown material by dividing the sum of the whole and the fractional amounts of observation points identified as each substance by the total number of observation points identified as any of said known substances.

18. The method of claim 17 wherein said process of using confidence measure comprises the steps of calculating the value of a confidence measure equation for said candidate substance and comparing said value to a threshold value, wherein said candidate substance is defined by the equation:

$$\prod_{j=1}^{m} (\mu_{k,j}(x_{s,j})) = \max_{i=1}^{n} \left( \prod_{j=1}^{m} (\mu_{i,j}(x_{s,j})) \right)$$

and said confidence measure is defined by the equation:

$$CM_k = \left[ \sum_{i=1}^{n} \left( \frac{\sum_{j=1}^{m} \left( \frac{d_{k,j}^2}{\sigma_{k,j}^2} \right)}{\sum_{j=1}^{m} \left( \frac{d_{i,j}^2}{\sigma_{i,j}^2} \right)} \right) \right]^{-1}$$

where k=the value of i that represents the candidate substance, $\mu_{i,j}(x_{s,j})$=1.0, if $x_{i,j}^{min} \leq x_{s,j} \leq x_{i,j}^{max}$ $\mu_{i,j}(x_{s,j})=f_{i,j}^{a}(z)$ if $x_{s,j} \leq x_{i,j}^{min}$ where, $z=(x_{i,j}^{min}-x_{s,j})$ and, $f_{i,j}^{a}(z) \leq 1.0$ and decreases as z increases $\mu_{i,j}(x_j)=f_{i,j}^{b}(z)$ if $x_{s,j} > x_{i,j}^{max}$ where, $z=(x_{s,j}-x_{i,j}^{max})$ and, $$f_{i,j}^b(z) \leq 1.0$$

and decreases as z increases

"m" is an integer defining the number of elements in the x-ray spectra,

"n" is an integer defining the number of substances in the database,

"i" is an integer from 1 to n identifying the subscripted variable as associated with a specific substance from said pre-selected set of substances, "j" is an integer from 1 to m identifying the subscripted variable as associated with a specific element from said pre-selected set of elements, "k" is the value of i associated with the candidate substance, "s" in superscripts indicates that the value of the subscripted variable is associated with said unknown material, "x" is an x-ray spectrum intensity value, $$d_{k,j} = \text{minimum}\ (|x_{s,j} - x_{k,j}^{max}|, |x_{s,j} - x_{k,j}^{min}|),$$

$$d_{i,j} = \text{minimum}\ (|x_{s,j} - x_{i,j}^{max}|, |x_{s,j} - x_{i,j}^{min}|),$$

$$\sigma_{i,j} = 1.5\sqrt{0.5(x_{i,j}^{max} + x_{i,j}^{min})}\,,$$

$$\sigma_{k,j} = 1.5\sqrt{0.5(x_{k,j}^{max} + x_{k,j}^{min})}\,, \quad \text{and}$$

"CM" is the confidence measure.

19. The method of claim 18 wherein $f_{i,j}^a(z)$ and $f_{i,j}^b(z)$ are normally distributed probability functions having a standard deviation, $\sigma_{i,j}$, defined by the equation $$\sigma_{i,j} = 1.5\sqrt{0.5(x_{i,j}^{max} + x_{i,j}^{min})}\,.$$

* * * * *